(12) United States Patent
Gibson et al.

(10) Patent No.: US 7,167,819 B1
(45) Date of Patent: Jan. 23, 2007

(54) METHOD OF DETERMINING THE THREE-DIMENSIONAL SHAPE OF A MACROMOLECULE

(75) Inventors: Bradford W. Gibson, Berkeley, CA (US); Irwin D. Kuntz, Greenbrae, CA (US); Ning Tang, San Francisco, CA (US); Gavin Dollinger, San Francisco, CA (US); Connie M. Oshiro, Mountain View, CA (US); Judith C. Hempel, San Francisco, CA (US); Eric W. Taylor, Oakland, CA (US); Malin Young, Newark, CA (US)

(73) Assignees: Chiron Corporation, Emeryville, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 09/580,380

(22) Filed: May 26, 2000

Related U.S. Application Data

(60) Provisional application No. 60/135,891, filed on May 26, 1999.

(51) Int. Cl.
| | |
|---|---|
| G06G 7/58 | (2006.01) |
| G01N 31/00 | (2006.01) |
| G01N 24/00 | (2006.01) |
| G12P 19/42 | (2006.01) |

(52) U.S. Cl. .......................... 703/12; 702/27; 435/86; 436/173
(58) Field of Classification Search .................. 702/19, 702/27
See application file for complete search history.

(56) References Cited

U.S. PATENT DOCUMENTS

| 5,045,694 A | 9/1991 | Beavis et al. |
| 5,160,840 A | 11/1992 | Vestal |
| 5,627,369 A | 5/1997 | Vestal et al. |

OTHER PUBLICATIONS

Jan Drenth, Principles of Protein X-ray Crystallography, 1995, Springer-Verlag, p. 16.*
News Focus, Science, Nov. 1, 2002, vol. 298, pp. 948-950.*
Nguyen et al., "Protein Mass Spectrometry: Applications to Analytical Biotechnology," Journal of Chromatography A. 705 (1995) 21-45.
Fischer et al., "XP002906968, Protein Fold Recognition Using Sequence-Derived Predictions," Protein Science (1996), 5:947-955.
Cohen et al. "On the Use of Chemically Derived Distance Constraints in the Prediction of Protein Structure with Myoglobin as an Example." *J Mol. Biol.* 1980 137:9-22.
Mitra et al. "Reagents for the cross-linking of proteins by equilibrium transfer alkylation." *J. Am. Chem. Soc.* 1979 101, 3097. For example, amino acid surface accessability in proteins has been probed using selective chemical modifications followed by proteolytic digestion and mass spectrometry profiling, of the resulting modified (and unmodified) peptides.
Suckau et al. "Protein surface topology-probing by selective chemical modification and mass spectrometric peptide mapping." *Proc Natl Acad Sci USA*. Jun. 15, 1992; 89(12):5630-4.
Glocker et al. "Molecular characterization of surface topology in protein tertiary structures by amino-acylation and mass spectrometric peptide mapping." *Bioconjug. Chem.* Nov.-Dec. 5, 1994; 5(6):583-90.
Seielstad et al. "Analysis of the structural core of the human estrogen receptor ligand binding domain by selective proteolysis/mass spectrometric analysis." *Biochemistry*, Oct. 3, 1995; 34(39):12605-15.
Seielstad et al. "Molecular characterization by mass spectrometry of the human estrogen receptor ligand-binding domain expressed in *Escherchia coli.*" *Mol. Endocrinol.* Jun. 1995;5(6):647-58.
Zappacosta et al. "Surface Topology of Minibody by Selective Chemical Modifications and Mass Spectrometry." *Protein Sci.* Sep. 1997;6(9):1909-9.
Scaloni, et al. "Structural investigations on human erythrocyte acylpeptide hydrolase by mass spectrometric procedures." *J Protein Chem.* Apr. 1999;18(3):349-60.
Smith et al. "Probing the non-covalent structure of proteins by amide hydrogen exchange and mass spectrometry." *J. Mass Spectrom.* 1979 32(2): 135-146, 1997.
Papac et al. "Epitope mapping of the gastrin-releasing peptide/anti-bombesin monoclonal antibody complex by proteolysis followed by matrix-assisted laser desorption ionization mass spectrometry." *Protein Sci.* Sep. 1994;3(9):1485-92.
Cohen et. al. "Probing the solution structure of the DNA-binding protein Max by a combination of proteolysis mass spectrometry," *Protein Sci.* Jun. 4, 1995; (6):1088-99.
Gomes et al. Proteolytic mapping of human replication protein A: evidence for multiple structural domains and a conformational change upon interaction with single-stranded DNA. *Biochemistry*. Apr. 30, 1996; 35(17):5586-95.

(Continued)

*Primary Examiner*—Marjorie A. Moran
*Assistant Examiner*—Lori A. Clow
(74) *Attorney, Agent, or Firm*—James E. Austin; Young J. Suh; Alisa A. Harbin

(57) ABSTRACT

The present invention provides a fast and efficient method for determining the three-dimensional conformation of a protein. The steps of the method of the invention include: 1) formation of physical distance constraints, e.g., forming intramolecular chemical crosslinks of known size between residues of a protein; 2) enriching the number of the molecules that have intramolecular chemical crosslinks in the reaction pool, e.g., using size separation to remove proteins with intermolecular bonds; 3) exposing the enriched reaction pool to a protease that cuts the protein at specific sites to produce peptide fragments; 4) measuring the size of the peptide fragments to determine linkage sites with a certain spatial relationship in the protein; and 5)interpreting the data produced to determine spatial geometry and protein structure based on the deduced spatial relationship of the linkage sites. The information is preferably analyzed with aid from a computer system, which can be used to generate and/or analyze distance constraints between amino acids.

21 Claims, 23 Drawing Sheets

OTHER PUBLICATIONS

Zappacosta et al. "Probing the tertiary structure of proteins by limited proteolysis and mass spectrometry: the case of Minibody," *Protein Sci.* May 1996; 5(5):802-13.

Gervasoni et al. "Identification of the binding surface on beta-lactamase for GroEL by limited proteolysis and MALDI-mass spectrometry." *Biochemistry*, Aug. 18, 1998; 37(33):11660-9.

Moore et al. "Proteolytic fragments of the nicotinic acetylcholine receptor identified by mass spectrometry: implications for receptor topography." *Biochemistry.* Nov. 14, 1989; 28(23):9184-91.

Massotte D, et al. "Structure of the membrane-bound form of the pore-forming domain of colicin A: a partial proteolysis and mass spectrometry study." *Biochemistry*, Dec. 21, 1993; 32(50):13787-94.

Havel et al. "Effects of Distance Constraints on Macromolecular Conformation. II. Simulation of Experimental Results and Theoretical Predictions." *Biopolymers.* 1979 18:73-81.

Lacroix et al. "Structure and assembly of the catalytic region of human complement protease C1r: a three-dimensional model based on chemical cross-linking and homology modeling." *Biochemistry*, May 27, 1997; 36(21):6270-82.

Dyda et al. "Crystal structure of the catalytic domain of HIV-1 integrase: similarity to other polynucleotidyl transferases," *Science*, Dec. 23, 1994; 266(5193):1981-6.

Lodi et. al. "Solution structure of the DNA binding domain of HIV-1 integrase." *Biochemistry*, Aug. 8, 1995; 34(31):9826-33.

Goldgur et. al. "Three new structures of the core domain of HIV-1 integrase: an active site that binds magnesium." *Proc Natl Acad Sci USA*, Aug. 4, 1998; 95(16):9150-4.

Havel et al. "An evaluation of the combined use of nuclear magnetic resonance and distance geometry for the determination of protein conformations in solution." *J Mol Biol.* Mar. 20, 1985; 182(2):281-94.

Guntert et al. "Improved efficiency of protein structure calculations from NMR data using the program DIANA with redundant dihedral angle constraints." *J Biomol NMR*, Nov. 1991;1(4):447-56.

Grant et al., "Edman Sequencing as Tool for Characterization of Synthetic Peptides," *Methods Enzymol.* 1997 289:395-419.

Lennon et. al., *Proceedings of the 42nd ASMS Conference on Mass Spectrometry and Allied Topics*, May 29-Jun. 3, 1994, Chicago, Illinois, p. 501.

Breuker et al., *13th International Mass Spectrometry Conference*, Aug. 29-Sep. 3, 1994, Budapest, Hungary.

Reilly et al., "Improving the Resolution of Matrix-assisted Laser Desorption/Ionization Time-of-flight Mass Spectrometry by Exploiting the Correlation between Ion Position and Velocity," *Rapid Commun.*, Mass Spectrometry, 8, 1994, 865-868.

Fenn et al., "Electrospray Ionization-Principle and Practice," *Mass Spectrom. Rev.*, vol. 9, pp. 37-70 (1990).

P. Kebarle et al., "From Ions in Solution to Ions in the Gas Phase," *Anal. Chem.*65: 972A-986A (1993).

Havel, et al. "The Combinatorial Distance Geometry Method for the Calculation of Molecular Conformation. I. A New Approach to an Old Problem", J Theor Biol. 104:359-81 (1983).

Alexandrov et al. "Fast Protein Fold Recognition via Sequence to Structure Alignment and Contact Capacity Potentials." *Protein Science Bulletin.* (1996).

Bryant et al. "An Empirical Energy Function for Threading Protein Sequence Through the Folding Motif," *Proteins*, 1993 16 92-112.

Murzin et al. "SCOP: a Structural Classification of Proteins Database for the Investigation of Sequences and Structures," *J Mol Biol.* Apr. 7, 1995; 247(4):536-40.

Venkataraman et al. "Preferential self-association of basic fibroblast growth factor is stabilized by heparin during receptor dimerization and activation." *Proc Natl Acad Sci USA*, Jan. 23, 1996; 93(2):845-50.

Haniu et al. "Recombinant human erythropoietin (rHuEPO): cross-linking with disuccinimidyl esters and identification of the interfacing domains in EPO." *Protein Sci.* Sep. 1993;2(9):1441-51.

Laemmli. "Cleavage of structural proteins during the assembly of the head of bacteriophage T4," *Nature.* Aug. 15, 1970;227(259):680-5.

Kaufmann et al. "Mass spectrometric sequencing of linear peptides by product-ion analysis in a reflectron time-of-flight mass spectrometer using matrix-assisted laser desorption ionization," *Rapid Commun Mass Spectrom.* Oct. 1993;7(10):902-10.

Holm et al. "Protein Structure Comparison by Alignment of Distance Matrices." *J Mol Bio.* 1993 233:123-38.

Hilbert et al. "Structural relationships of homologous proteins as a fundamental principle in homology modeling." *Proteins.* 1993 17(2):138-51.

Tullius et. al. "Covalent modification of Lys19 in the CTP binding site of cytidine 5'-monophosphate N-acetylneuraminic acid synthetase." *Protein Sci.* Mar. 1999;8(3):666-75.

Samules, et al. "Investigation of the Kinetic Mechanism of Cytidine 5'-Monophosphate N-Acetylneuraminic Acid Synthetase from *Haemophilus ducreyi* With New Insights On Rate-limiting Steps from Product Inhibition Analysis." *Biochemistry*, 1999 38(19) 6195-203.

Rossi et al. "Structure of the catalytic region of human complement protease C1s: study by chemical cross-linking and three-dimensional homology modeling." *Biochemistry*, Jun. 6, 1995; 34(22):7311-21.

* cited by examiner

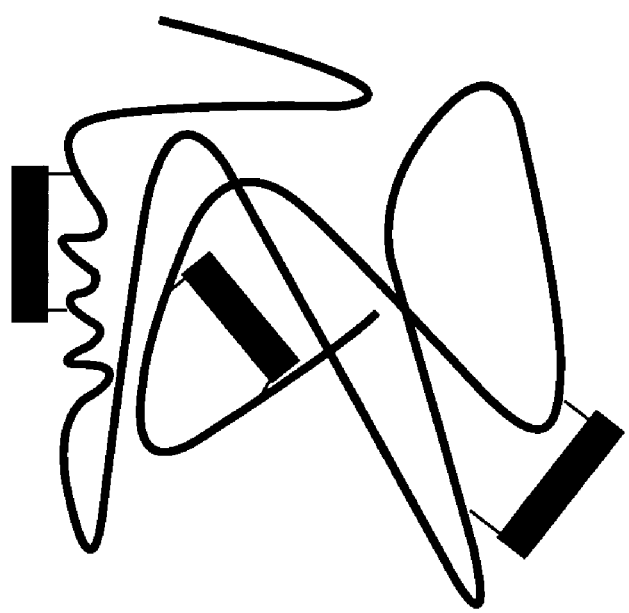
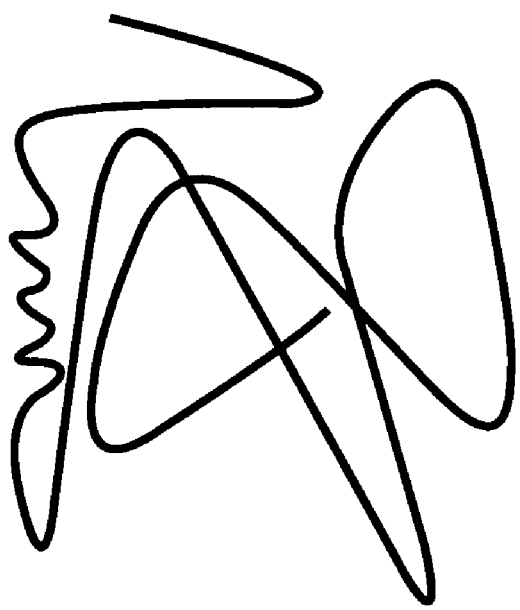
FIGURE 4

SUMMARY REPORT

INTRAFRAGMENT ASSIGNMENTS
Mass        Assignment      # Peaks    PPM Error    Crosslink

. . .

1000.24     1-10            3          4.3          5-8
1000.37     38-50           2          3.7          40-44
1000.96     57-66           2          4.4          55-61

. . .

INTERFRAGMENT ASSIGNMENTS
Mass        Assignment      # Peaks    PPM Error    Crosslink

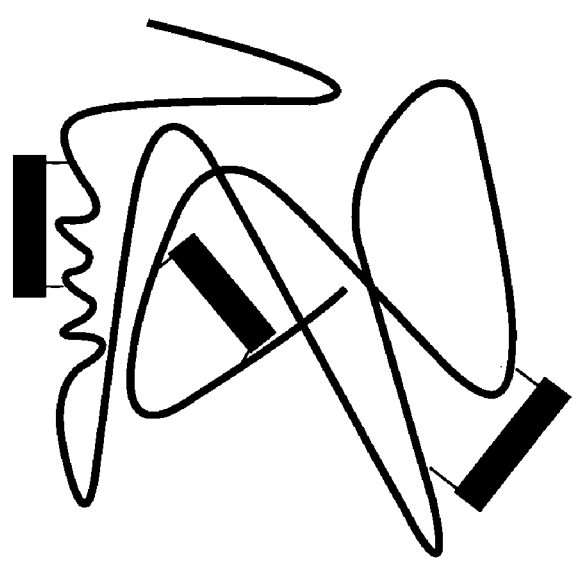
Proteolysis
FIGURE 11

A)
IL-1β    1 ------APVRSLNCTLRDSQQKSLMVMSGPYELKALHLQ--GQDMEQQVVFSMSFVQGE
FGF2    1 PALPEDGGSGAFPPGHFKDPK-RLYCKNGGFFLRIHPDGRVDGVREKSDHIK---LQLQ

IL-1β   61 ESNDKIPVALGKEKNLYLSCVLKDDKPTLQLESVDPKNYPKKKMEKRFVFNKIEINNKL
FGF2   61 AEERGVVSIKGVCANRYL--AMKEDGRLLASK------CVTDECFFFERLESNNYN

IL-1β  121 EFESAQFPNWYISTSQAENMPVFLGGTKGGQDITDFTMQF--VSS
FGF2  121 TYRSRKYSSWYVALKRTGQY---KLGPKTGPGQKAILFLPMSAKS

B)
IL-1β    1 APVRSLNCTLRDS--QQKSLMVMSGPYELKALHLQGGQDMEQQ- VVFSMSFVQGEESNDKIPV
FGF2    1 ------PKRLYCKNGGFFLRIHPDGRVDVRE----KSDPHIKLQLQAEE------ RGVV

IL-1β   61 ALGKEKNLYLSCVLKDDKPTLQLESVDPKNYPKKKMEKRFVFNKIEI-NNKELFESAQF
FGF2   61 SIKGVCANRYLAMKE--DGRLLASKC------VTDECFFFERLESNNYNTYRSRKY

IL-1β  121 PNWYISTSQAENMPVFLG-GTKGGQDITDFTMQFVSS
FGF2  121 SSWYVALKRT-GQYKLGPKTGPG-QKAILFLPMSAKS

FIGURE 20

FGF-2 Crystal Structure (4fgf)
Homology model based on IL-1β

METHOD OF DETERMINING THE THREE-DIMENSIONAL SHAPE OF A MACROMOLECULE

CROSS-REFERENCE TO RELATED APPLICATION

The current U.S. patent application claims priority to U.S. Provisional Patent Application No. 60/135,891, "Method of Determining the Three-Dimensional Shape of a Structure," filed May 26, 1999. This patent application is herein incorporated by reference in its entirety for all purposes, along with any other patents and publications referenced in this application.

This application was made in part with government support under contract numbers GM31497 and AI31254 awarded by the National Institutes of Health. The government has certain rights in the invention.

FIELD OF THE INVENTION

This invention relates generally to methods of analyzing macromolecular structures. More particularly, the invention relates to a method for determining the three-dimensional structure of proteins and other biopolymers using an integration of chemical manipulation, mass determination, and computer modeling.

BACKGROUND OF THE INVENTION

The revolution in our ability to determine the three-dimensional structures of biological macromolecules began with X-ray diffraction analysis of crystals and then was extended to the use of high-resolution magnetic resonance for proteins in non-crystalline environments. These methods have been enormously successful, and thousands of structures are now deposited in the Brookhaven Protein Databank and Nucleic Acid Databank. Often such techniques are used for rational drug design. These techniques often take many years, however, and require a sufficient amount of a pure product to allow proper analysis of the protein.

Despite the success of crystallographic and magnetic resonance approaches such as NMR in tertiary structure determination, there remain much larger numbers of proteins and nucleic acid whose structures are not known and where success remains problematic, e.g., membrane proteins and proteins with insufficient solubility for crystal formation. In addition, the various genome projects promise to identify tens of thousands of new proteins in the next few years alone that will undoubtedly create a backlog of undetermined structures that will require new high-throughput strategies if scientists are to take advantage of this vast new sequence information.

One approach that has been examined as an alternative to NMR or crystallography is chemical crosslinking. Crosslinking and monovalent labeling experiments have been carried out for many years and can provide low-resolution structural information. Cohen et al. "On the Use of Chemically Derived Distance Constraints in the Prediction of Protein Structure with Myoglobin as an Example." *J. Mol. Biol.* 1980 137:9–22; Mitra et al. "Reagents for the cross-linking of proteins by equilibrium transfer alkylation." *J. Am. Chem. Soc.* 1979 101, 3097. For example, amino acid surface accessibility in proteins has been probed using selective chemical modifications followed by proteolytic digestion and mass spectrometry profiling, of the resulting modified (and unmodified) peptides. Suckau et al. "Protein surface topology-probing by selective chemical modification and mass spectrometric peptide mapping." *Proc Natl Acad Sci USA.* 1992 Jun. 15;89(12):5630–4; Glocker et al. "Molecular characterization of surface topology in protein tertiary structures by amino-acylation and mass spectrometric peptide mapping." *Bioconjug. Chem.* 1994 Nov.–Dec.;5 (6):583–90; Seielstad et al. "Analysis of the structural core of the human estrogen receptor ligand binding domain by selective proteolysis/mass spectrometric analysis." *Biochemistry.* 1995 Oct. 3;34(39):12605–15; Seielstad et al. "Molecular characterization by mass spectrometry of the human estrogen receptor ligand-binding domain expressed in *Escherichia Coli.*" *Mol. Endocrinol.* 1995 Jun.;9(6): 647–58; Zappacosta et al. "Surface Topology of Minibody by Selective Chemical Modifications and Mass Spectrometry." *Protein Sci.* 1997 Sep.;6(9):1901–9; Scaloni, et al. "Structural investigations on human erythrocyte acylpeptide hydrolase by mass spectrometric procedures." *J Protein Chem.* 1999 Apr.;18(3):349–60.

Amide hydrogen exchange experiments with subsequent proteolysis and mass spectrometry have also been used to map solvent accessible regions in protein structures Smith et al. 1997; Smith et al. "Probing the non-covalent structure of proteins by amide hydrogen exchange and mass spectrometry." *J. Mass. Spectrom.* 1979 32(2): 135–146. 1997. Susceptibility to proteolysis has been employed by several groups as a measure of site accessibility, which indirectly identifies amino acid regions as exposed or buried. Papac et al. "Epitope mapping of the gastrin-releasing peptide/anti-bombesin monoclonal antibody complex by proteolysis followed by matrix-assisted laser desorption ionization mass spectrometry." *Protein Sci.* 1994 Sep.;3(9):1485–92; Cohen et. al. "Probing the solution structure of the DNA-binding protein Max by a combination of proteolysis mass spectrometry." *Protein Sci.* 1995 Jun.;4(6):1088–99; Gomes et al. "Proteolytic mapping of human replication protein A: evidence for multiple structural domains and a conformational change upon interaction with single-stranded DNA. *Biochemistry.* 1996 Apr. 30;35(17):5586–95; Zappacosta et al. "Probing the tertiary structure of proteins by limited proteolysis and mass spectrometry: the case of Minibody." *Protein Sci.* 1996 May;5(5):802–13; Gervasoni et al. "Identification of the binding surface on beta-lactamase for GroEL by limited proteolysis and MALDI-mass spectrometry." *Biochemistry.* 1998 Aug. 18;37(33):11660–9. Both proteolytic and acylation approaches have been applied to characterize the topology of integral membrane proteins, such as the acetylcholine receptor, for which one would expect to observe distinct patterns for cytoplasmic, extracellular and membrane spanning elements. Moore et al. "Proteolytic fragments of the nicotinic acetylcholine receptor identified by mass spectrometry: implications for receptor topography." *Biochemistry.* 1989 Nov. 14;28(23):9184–91.; Massotte D, et al. "Structure of the membrane-bound form of the pore-forming domain of colicin A: a partial proteolysis and mass spectrometry study." *Biochemistry.* 1993 Dec. 21;32(50):13787–94. However, one of the major limitations of these labeling strategies has been the lack of methods for rapid and unambiguous identification of the protein modifications. Further, these types of labels are of little use in determining over-all structure.

There are also several purely computational methods for predicting a protein's fold that have been examined as potential alternatives to deducing chemically the tertiary structure of a protein. However, none of these computational methods are reliable. Twenty years ago, one study showed that low-resolution distance information could determine a protein structure with distance geometry. Havel et al. "Effects of Distance Constraints on Macromolecular Conformation. II. Simulation of Experimental Results and Theoretical Predictions." *Biopolymers.* 1979 18:73–81. Havel et al. reconstructed the alpha carbon backbones of bovine pancreatic trypsin inhibitor (PTI) and carp calcium-binding protein-B (carp myogen) to within 1 Å RMS of the experimentally determined structures by specifying whether each alpha carbon was closer or further than 10 Å from all other alpha carbons in the structure and using distance geometry to solve for structures which satisfied the constraints. Despite the obvious implications of this theoretical demonstration, there has been little progress in experimental approaches that might provide the required distance constraints, short of NMR and/or X-ray crystallography itself.

There is thus a need in the art for a fast, high-throughput method for determining the tertiary structure of a protein. There is also a need for methods that can provide at least a moderate resolution determination of protein structure with small amounts of protein without the need for extensive purification processes. In addition, there is a need for improved methods to orient multimeric proteins or domains.

SUMMARY OF THE INVENTION

The present invention provides a fast and efficient method for determining the three-dimensional structure or conformation of a protein or other macromolecule. The steps of the method of the invention include: 1) generating physical distance constraints, e.g., forming intramolecular chemical crosslinks of known length between residues of a protein; 2) enriching the number of the molecules that have intramolecular chemical crosslinks in the reaction pool, e.g., by size separation to remove proteins with intermolecular bonds; 3) exposing the enriched reaction pool to one or more protease that proteolyzes the protein at specific or non-specific sites to produce peptide fragments; 4) identifying the peptide fragments to determine linkage sites with a certain spatial relationship in the protein; and 5) interpreting the data produced to determine spatial geometry and protein structure based on the deduced spatial relationship of the linkage sites. The information is preferably analyzed with aid of a computer system, which can be used to generate and/or analyze distance constraints and spatial geometry between domains and/or folds within a protein. The obtained data is optionally compared to proteins of known structure, and structural modeling using techniques such as threading can be employed to aid in the determination of protein folding. The combined use of these techniques provides a surprisingly accurate 3-dimensional chemical structure much more quickly and efficiently than other conventional methods used currently in the field.

The chemical reagent used to form intramolecular crosslinks in a protein preferably will react with at least one predicted residue in the protein, e.g., at least one end of the chemical crosslinking residue will bind to a predicted site on the protein, such as any two e-amino groups within a lysine within the protein. In a preferred embodiment of the invention, the chemical reagent used for crosslinking the protein will react with two predicted functional sites on a protein, e.g., the crosslinking reagent will crosslink any two lysine residues in the protein.

An aspect of the invention is a method of analyzing molecules such as proteins in a manner which results in obtaining information regarding the three-dimensional (tertiary) structure of the protein. Some proteins cannot be crystallized and so cannot be analyzed by X-ray crystallography. Membrane proteins are examples of proteins that are difficult or impossible to crystallize. Many proteins are not soluble enough to use NMR. The current invention is applicable to essentially all proteins.

In another aspect of the invention, a system for determining information the structural details of a molecule is provided, the system including a mass spectrometer, and a computational system that accepts mass information from the mass spectrometer and outputs structural details of the molecule by processing that information. The system can provide structural details of polypeptides, nucleic acids and other macromolecules. The molecule has at least one distance constraint placed on it, in the case of a polypeptide, often a crosslinker such as BS3 (Bis[sulfosuccinimidyl] suberate). The number of constraints imposed on the polypeptide can be less than about 20% of the number of amino acid residues. The system also carries out constrained threading and homology modeling in order to output a three-dimensional structure of the macromolecule. In another aspect of the invention, just the computational system for carrying out these same procedures and outputting structural details of the molecule is provided. The computational system accepts information from another source, such as a mass spectrometer, in order to do this.

In another aspect of the invention, a computer-implemented method for scoring candidates of a molecule is provided, including the steps of accepting mass information, generating or storing expected fragments of the molecule, matching the mass information to the expected fragments, and scoring the candidates. The system can provide structural details of polypeptides, nucleic acids and other macromolecules. The molecule has at least one distance constraint placed on it, in the case of a polypeptide, often a crosslinker such as BS3 (Bis[sulfosuccinimidyl] suberate). The number of constraints imposed on the polypeptide can be less than about 20% of the number of amino acid residues. In another aspect of the invention, a computer-program product is provided for carrying out these scoring procedure.

In one embodiment of the invention, amino acids of the protein such are crosslinked using a detectably labeled crosslinking agent.

An advantage of the invention is that the compounds can be more quickly analyzed as compared to conventional three-dimensional analytical methods. Also, this technique is applicable to intrinsically heterogeneous proteins such as glycosylated proteins.

Another advantage of the invention is that the protein to be studied does not need to be as pure as for NMR or X-ray crystallography.

Yet another advantage is that less protein is needed for analysis than for analysis using NMR or X-ray crystallography.

Yet another advantage is that the protein concentration used in the methods of the invention are preferably dilute.

These and other objects, aspects, advantages, and features of the invention will become apparent to those persons skilled in the art upon reading the details of the methodology as more fully described below.

BRIEF DESCRIPTION OF THE DRAWINGS

FIG. 4 is a schematic depiction of the formation of physical distance constraints in a protein using chemical crosslinking.

FIG. 8 is a schematic illustration of a user report of the results from the computational process of FIG. 6.

FIG. 11 is a schematic depiction of the proteolysis of the crosslinked protein.

FIG. 20 (part a) shows a threading alignment of interleukin-1β(IL-1β SEQ ID NO:6) and FGF-2 (FGF2 SEQ ID NO:7) used for homology modeling. Insertions are indicated by dashes. The bars above and below the alignment show the beta strand positions in interleukin-1β (above) and FGF-2 (below) as defined in the PDB structure files. The sequence alignment identity is 12.7%. FIG. 18 (part b) also shows DALI structural alignment of IL-1β and FGF-2. The structural root-mean-square deviation (RMSD) of the DALI alignment is 2.7 Å over 101 residues.

DETAILED DESCRIPTION OF PREFERRED EMBODIMENTS

Figure 1:
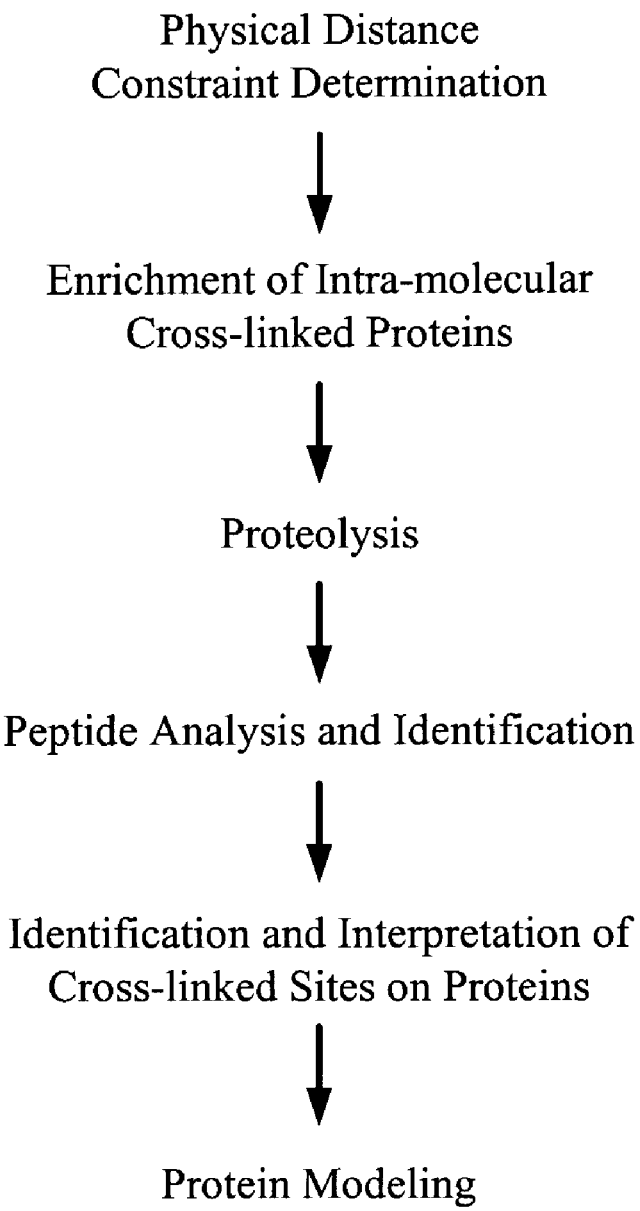
FIG. 1 is a flow chart illustrating the integral steps of the methods of the invention.

Before the present methods of modeling are described, it is to be understood that this invention is not limited to particular protocols described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The terms "crosslinker," "crosslinking reagent," and the like as used interchangeably herein refer to any reagent that chemically links amino acids in a protein that are in sufficient proximity to allow reaction between reactive sites on two or possibly more amino acids. The crosslinker has the ability to react with reactive functional groups on a protein that are within a maximum distance for that particular crosslinker, wherein the reactive groups (X and/or Y) are designed to react in a specific or general manner with various functional groups present on the amino acid side chains. A bifunctional crosslinker can be homobifunctional (X—X or Y—Y) where the reactive groups are the same, or heterobifunctional where the reactive groups are different (X—Y). Examples of amine-specific homobifunctional linkers are BS3 (Bis[sulfosuccinimidyl] suberate) and sulfo-DSP (Dithiobis(succinimidylpropionate]). The functional groups X and/or Y may be any functional site on an amino acid that will chemically react with a crosslinker, e.g., an γ-amine or methylene. An example of an amine-specific and methylene-specific heterobifunctional macromolecule is SAND (Sulfosuccininzidyl 2-[ozido-o-nitro-benzamido] ethyl-1,3'dithiopropionate) which has an arylazide, a photoactivatable group specific for insertion into C—H bond as the second and orthogonal reactive sites.

The term "trifunctional crosslinker" as used herein refers to any macromolecule that, in addition to containing two amino acid-specific reactive groups, also contains a third group, for example, an affinity group that allows for ease of purification of the linked peptides. For example, one commercially available trifunctional crosslinker, Sulfo-SBED (Sulfosuccinimidyl [2-o-(biotinamido)-2-(p-azidobenzamido)-hexamido] ethyl 1,3'-dithiopropionate) has a biotin group, which can be affinity selected using avidin.

The term "on-line chromatography-mass spectrometry" as used herein refers to a method by which a chromatography effluent flows into a mass spectrometer. The effluent may directly flow into the spectrometer, or alternatively may flow through other detection means prior to entering the mass spectrometer.

The term "off-line chromatography" as used herein refers to a method by which chromatography is performed, fractions are separated, and subsequently analyzed.

The term "low resolution" as used herein refers to resolution of structures above about 5 Å.

The term "moderate resolution" as used herein refers to structures between about 2–5 Å. The invention herein can provide resolution of structures between about 2–5 Å, and more usually about 3–5 Å.

GENERAL ASPECTS OF THE INVENTION

The present invention is based on the finding that the integrated technique of determining physical distance constraints and analysis of the constraint information can reliably yield sufficient amino acid proximity information to allow the determination of the structural aspects of a macromolecule to a level of resolution between about 3 Å to about 5 Å, and more particularly between about 3.5 Å to 4.5 Å. For ease of description, the technique is described herein in terms of determining spatial geometry of a protein. This technique may be used to determine structural aspects of other macromolecules as well, e.g., structural relationships of RNA, DNA and/or the relationship of interactions of these molecules with proteins (e.g., regulatory binding) and the methods of the invention are not meant to be limited to determining protein structure. Accordingly, although the following disclosure is directed to using the methods of the present invention to determine the tertiary structure of a protein, it is understood that the same general concepts are applicable to identifying structures of a wide range of different types of macromolecules.

FIG. 1 illustrates the steps in one embodiment of the method of the present invention. The first step in the method of the invention, physical distance constraint determination, involves identification of spatial constraints of a protein using chemical or physical means. One embodiment of the invention utilizes chemical crosslinking agents to determine limits on the spatial relationship of residues in a protein. Since only residues having functional groups compatible with the crosslinker and having proximity to allow chemical reaction will actually crosslink, identification of crosslinked residues can be used to determine the geometric constraints on the conformation of the protein. Multiple crosslinkers with different spatial constraints and/or functional group specificities may be used in the determination of a protein structure.

The second step in the method of the invention is enrichment of the crosslinked reaction pool for intra-molecular crosslinked proteins. Following crosslinking, the reaction pool is enriched for proteins with intrapeptide crosslinks, and preferably the molecules with interpeptide bonds are removed completely, e.g., by a size separation technique.

The third step in the method of the invention is proteolysis of the enriched reaction pool. The crosslinked peptides are subject to proteolysis with a proteolytic enzyme that reacts with at a known cleavage site, e.g., trypsin. The crosslinked fragments will remain connected following proteolysis, and since the number of peptide fragments can be predicted for the protein before it is crosslinked, determination of the sizes of fragments produced after proteolysis of the crosslinked protein will allow identification of the residues that react with a certain-sized chemical crosslinking reagent.

The fourth step in the method of the invention is the analysis of the peptide fragments produced by proteolysis. In one embodiment of the invention, mass spectrometry (MS) techniques are used to identify the crosslinked fragments. With the advent of readily available, high-resolution, mass spectrometry techniques, such as time-of-flight (TOF) mass spectrometry, and tandem mass spectrometry (MS/MS), it has become feasible to analyze complex mixtures of components such as the peptides that arise from proteolytically-digested crosslinked proteins. MS technology permits the resolution of molecular ions at the isotopic level with a high degree of mass accuracy (<10 ppm) for large numbers of crosslinks.

The final step of the methods of the invention involves protein modeling, and particularly modeling using spatial geometry software. The high sensitivity and mass range of more modern mass spectrometry methods used in conjunction with protein modeling techniques, e.g., homology modeling, allow domain-mapping and the construction of moderate-resolution structures, i.e. structures between about 3 Å to 5 about Å. Integration and interpretation of this data can determine the structural conformation of the protein, and thus is indicative of the tertiary structure of the protein.

The structural questions that can be addressed by intramolecular crosslinking are not restricted to fold recognition. In the limit of few constraints, domain—domain placement can be done with ~3 constraints per domain pair. Rossi et al. "Structure of the catalytic region of human complement protease C1s: study by chemical cross-linking and three-dimensional homology modeling." *Biochemistry.* 1995 Jun. 6;34(22):7311–21; Lacroix et al. "Structure and assembly of the catalytic region of human complement protease C1r: a three-dimensional model based on chemical cross-linking and homology modeling." *Biochemistry.* 1997 May 27;36 (21):6270–82. Thus, large proteins that have structures that can be solved at the domain level, for instance HIV-1 integrase can also be analyzed using the methods of the invention. In the limit of many constraints, protein structural calculations could be performed directly using distance geometry followed by molecular dynamics refinement. Dyda et al. "Crystal structure of the catalytic domain of HIV-1 integrase: similarity to other polynucleotidyl transferases." *Science.* 1994 Dec. 23;266(5193):1981–6; Lodi et. al. "Solution structure of the DNA binding domain of HIV-1 integrase." *Biochemistry.* 1995 Aug. 8;34(31):9826–33; Cai et. al. *Nat. Struct. Biol.* 1997 4, 567–77; Goldgur et. al. "Three new structures of the core domain of HIV-1 integrase: an active site that binds magnesium." *Proc Natl Acad Sci USA.* 1998 Aug. 4;95(16):9150–4; Havel et al. "An evaluation of the combined use of nuclear magnetic resonance and distance geometry for the determination of protein conformations in solution." *J Mol. Biol.* 1985 Mar. 20;182(2):281–94; Guntert et al. "Improved efficiency of protein structure calculations from NMR data using the program DIANA with redundant dihedral angle constraints." *J Biomol NMR.* 1991 Nov.;1(4):447–56.

The method of the invention has several advantages that give the method significant utility, especially in light of limitations in other techniques for determining protein structure available in the art. This method generates the first reliable modest resolution (3 to 5 Å) structure that can, in principle, be used as a starting point to refine X-ray crystallography and NMR data, saving considerable of time and effort. The method of the invention is relatively fast to employ, and so is particularly useful in analyzing large numbers of peptides quickly. The experimental protocol is fully automatable and is thus amenable to a high-throughput approach. Thus, the present invention is particularly suited to analyzing the results of genomic and proteomic studies. Intramolecular crosslinking is enhanced under conditions of very low protein concentrations, so only a small amount of protein is required. Protein purity is less critical for the methods of the present invention than for other techniques, such as NMR or X-ray crystallography, as only peaks consistent with crosslinked peptides, based on molecular weight and sequence information, are of interest. Specifically, the invention is applicable to obtaining tertiary structure in a relatively short period of time (ranging on average from one day to at the most several weeks) with a protein. The methods described herein can be used with arbitrary protein mixtures; such as, in one specific example, protein samples of only moderate purity (e.g., from greater than about 60% to greater than about 80% purity), as would be expected from a typical in vitro His-tagged protein expression system followed by simple one or two step purification.

Figure 2:
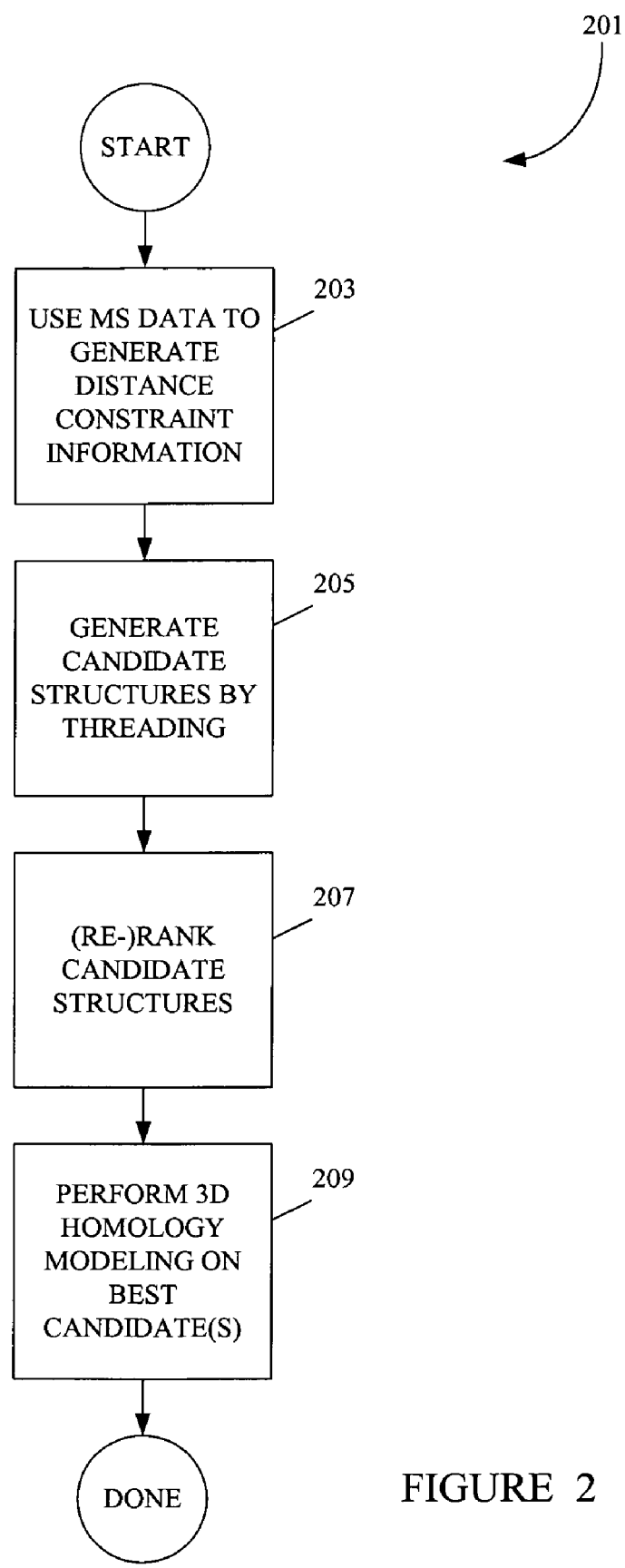
FIG. 2 is a high-level flowchart of the computational processes that are used in the invention.

In one aspect, various operations performed in executing the method of the present invention are carried out as computational processes. For example, various operations that interpret chemical data from a mass spectrometer and determine three-dimensional structural information from interpretations can be carried out computationally. FIG. 2 is a flowchart that gives a high-level overview of the computational features 201 of one embodiment of the invention. Step 203 involves the assignment of peptide fragment sequences to observed mass spectrometry peaks from the proteolyzed protein to generate distance constraint information by identifying protein fragments containing cross-linked residues. Step 205 involves the generation of a ranked list of candidate secondary structures by a threading approach. As explained in more detail below, threading involves laying out the primary sequence of the protein in question in a three-dimensional path following the layout of another protein having a known three-dimensional structure. Step 207 is a re-ranking of those candidate structures based on their compatibility with physical constraint criteria such as, but not limited to, (i) hydrophobic interactions between residues or (ii) the distance constraint information of step 203. Step 209 is application of homology modeling to the top candidate or candidates determined in step 207 to obtain a further refinement of the structure by positionally matching residues of the protein in question with residues of the top candidate.

Figure 3:
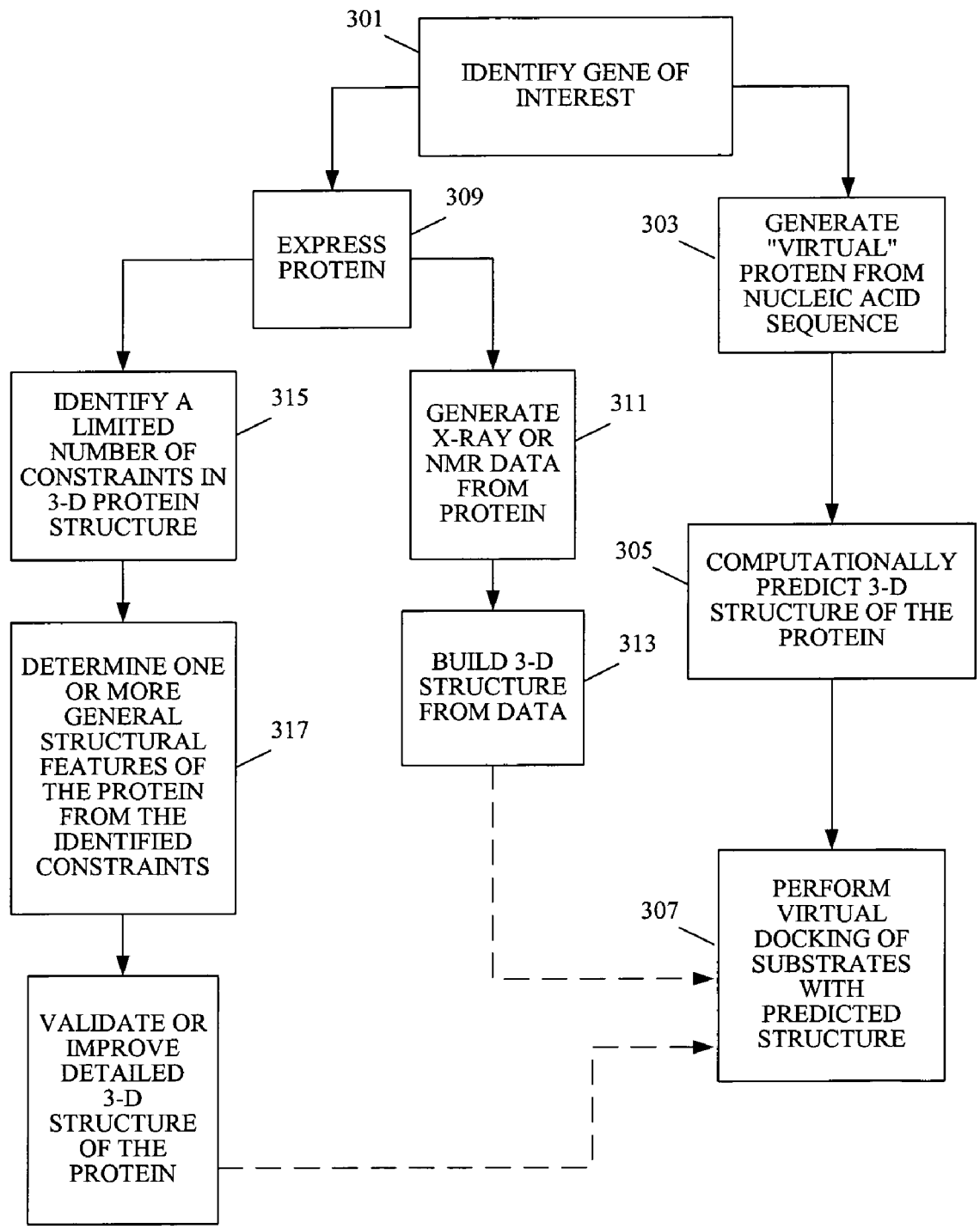
FIG. 3 is a flowchart illustrating how the present invention is used as part of a larger genomic or proteonomic investigation.

FIG. 3 illustrates how the present invention can be used as part of a larger genomic or proteonomic investigation for identifying, designing and/or analyzing proteins, particularly enzymes, or macromolecules that bind with such proteins. Three-dimensional protein structures may be generated in various manners. The two paths on the right side of FIG. 3 represent conventional techniques for analyzing proteins and generating protein structures from genomic data. Researchers typically begin by identifying or designing a gene/polynuclotide sequence. See 301. As part of an entirely in silico process (far right path), a virtual protein would then be generated from the primary nucleotide/amino acid sequence. See 303. Various well-known processes can then be used to predict the 3-D structure of the resulting protein. See 305. Such processes may be done entirely in silico starting only with the primary sequence of the protein, i.e., without using supplemental experimental data. At this point in time, entirely in silico techniques work well for predicting a protein's secondary structure, but are inadequate for predicting higher resolution features beyond the secondary structure. In any event, the predicted three-dimensional structure of the protein is then sometimes used to perform virtual experiments, such as virtual docking with ligands of interest. See 307. Such docking is only as useful as the protein structure is accurate. Similar docking experiments can be done with structures derived from the other two flow-chart paths.

With a given gene or nucleotide sequence in hand, an actual protein can of course actually be made. See 309. As discussed above, X-ray crystallography or NMR can then be performed on the actual protein (311) to predict its 3-D structure. See 313. Unfortunately, these methods have well-known difficulties and limitations. Both are extremely time consuming. X-ray crystallography requires crystalline samples of the protein in question, and many proteins do not crystallize. Among proteins that do crystallize, some assume non-native conformations when they do so. NMR often requires that the protein be suspended or dissolved in extremely concentrated salt solutions. Such conditions often perturb the native conformation of the protein. The present invention allows for the use of very limited empirical information in the form of cross-linking residues to obtain a very good prediction (within 2 to 5 Å RMS) of the actual 3-D structure of a protein. It has been found that a surprisingly small number of cross-links, typically about 10% of the number of amino acid residues, is adequate for purposes of the invention. See 315. This constraint information is then used to determine general structural features of the protein, 317, which is used to validate or improve 3-D structures that were determined entirely in silico or via NMR or X-ray crystallographic experiments.

Physical Distance Constraint Determination

Numerous techniques for determining physical distance constraints between residues in a protein may be employed, including fluorescence resonant energy transfer and spin-labeling techniques. In a preferred embodiment, distance constraints are determined by crosslinking the protein and then using mass spectroscopy to identify linked fragments. FIG. 4 is a schematic illustration of such a crosslinked protein. The crosslinker region can be a simple alkyl chain, and the length of the crosslinker can be varied, e.g., by varying the ethylene group. The crosslinker region may be short or long, and may define a more exact proximity (e.g., binding of a reagent with a rigid crosslinker region) or define an outer boundary for binding proximity (e.g., binding of a reagent with a flexible crosslinker region). The crosslinker can also be chemically modified to change other properties, e.g., a hydroxyl group can be added to make the crosslinker more hydrophilic or an aromatic group can be added to make the crosslinker more rigid. Many different linkers can be used in the methods of the invention, including bifunctional and trifunctional chemical crosslinkers. For any crosslinker, at least one, and preferably both, of the possible reactive sites are known. The reactive groups can be considered orthogonal or non-orthogonal relative to their reactivity.

To maximize the distance constraint information that can be extracted from crosslinking experiments, a more diverse set of amino acid functionalities can be targeted by a library of crosslinking agents with spacer arms of differing lengths and flexibilities. More rigid or shorter spacers narrow the range of possible distances between crosslinked residues, thereby providing more discrimination in fold recognition. Moreover, experiments performed with a library of crosslinkers can be used to improve the overall precision of the constraints. By providing more distance constraints for conformation analysis, the number and precision of the experimentally-derived constraints define the types of structural questions that can be answered. The crosslinking reagents used may be chosen using various factors known to those of skill in the protein and peptide chemistry arts, including predicted structural motifs in the protein, e.g., motifs that may be predicted from the primary sequence of the protein. If certain structural aspects of a protein are to be identified, e.g., screening of multiple proteins to identify specific domains and/or folds, then the crosslinking reagents may be selected based on their efficacy in identifying certain domains and/or folds.

Different crosslinkers with varying lengths, rigidity, specificity and the like can be employed, as will be apparent to one skilled in the art upon reading the present disclosure. For example, a series of homobifunctional reagents of variable lengths and/or specificity can be created to provide crosslinkers with appropriate lengths and/or chemical compositions suitable for study of a specific protein. For example, the study of a particular protein can be undertaken using a series of homobifunctional reagents of variable lengths with amine specificity. Crosslinkers homologous to the crosslinker BS3 (Bis[sulfosuccinimidyl] suberate), which has 6 methylenes, can be produced, e.g., crosslinkers with lengths of 2 and 4 methylenes, to provide a series of amine-specific crosslinkers with varying lengths. Combining data obtained using the various crosslinkers can provide a more detailed analysis of the spatial constraints of a protein.

Exemplary crosslinking reagents for use in the methods of the invention are EDC (1-Ethyl-3-[3-dimethylamniopropyl]-carbodiimide hydrochloride); DSP (Dithiobis [succinimidylpropionate]) also known as Lomant's reagent; BS3 (Bis[sulfosuccinimidyl] suberate) and DSS (Disuccinimidyl suberate). DSP and DSS are both homobifunctional, amine reactive agents differing only on the fact that the disulfide bond in DSP allows for it to be cleaved whereas DSS is non-cleavable. BS3 is a water soluble analogue of DSS that is membrane impermeable. EDC is versatile, being water soluble and capable of converting carboxyl groups (either Asp or Glu residues present in the target protein or carboxylic groups on the crosslinker) to their active esters and allowing for nucleophilic attack by amine-containing molecules (protein or crosslinker) to form a stable amide crosslinks.

To generate crosslinks in a protein, the selected crosslinker is added to the protein solution and allowed to react under conditions effective to allow crosslinking. The conditions, e.g., buffer, relative concentrations of protein and crosslinker, pH, temperature, time, and the like, are selected to be suitable for forming a covalent bond with its target functional amino acid groups, as can be predicted by one skilled in the art. In the case of a homobifunctional crosslinker (or homotrifunctional crosslinker, X-z-Y), both groups would be allowed to react and some percentage of the crosslinkers would form crosslinks between two spatially distinct amino acids on the same protein (intramolecular crosslink) or between two separated protein molecules (intermolecular crosslink). In the case of a heterobifunctional crosslinker, a second set of conditions would be subsequently employed for the orthogonal group to react with its target sites., e.g., light, in the case of a photoactivatable groups such as an arylazide, or a change in pH in the case of a sulfyldryl-selective group.

For example, BS3 and DST were found to react well under the following generic reaction conditions with FGF-2: 25° C., 2 hours, 5 µM protein with a 20:1 molar ratio of crosslinker to protein in 100 mM Hepes buffer, pH 7.5. Crosslinking reactions with HIV-1 integrase, which can be unstable at certain temperatures, was accomplished using a reduction in the reaction temperature with an increase in the overall reaction time (0° C., at 40 hours). A Lys-Cys heterobifunctional crosslinker, such as sulfo-EMCS (N-[ε-Maleimidocaproloxy] sulfosuccinimide ester) or sulfo-GMBS (N-[γ-Maleimidobutyryloxy]sulfo-succinimide ester) react with Lys through NHS-ester and Cys through maleimide functional groups. The maleimide group is most selective for sulfhydryl when the pH is between 6.5 to 7.5, and above this pH, the reaction with primary amines become more significant. This reaction can be carried out in one step at pH 7.0 for the NHS-ester and maleimide groups to react at the same time; or it can be separated in two steps, one at pH 6.5 for maleimide group and then a second step at pH 7.5 for NHS-ester.

Figure 5:
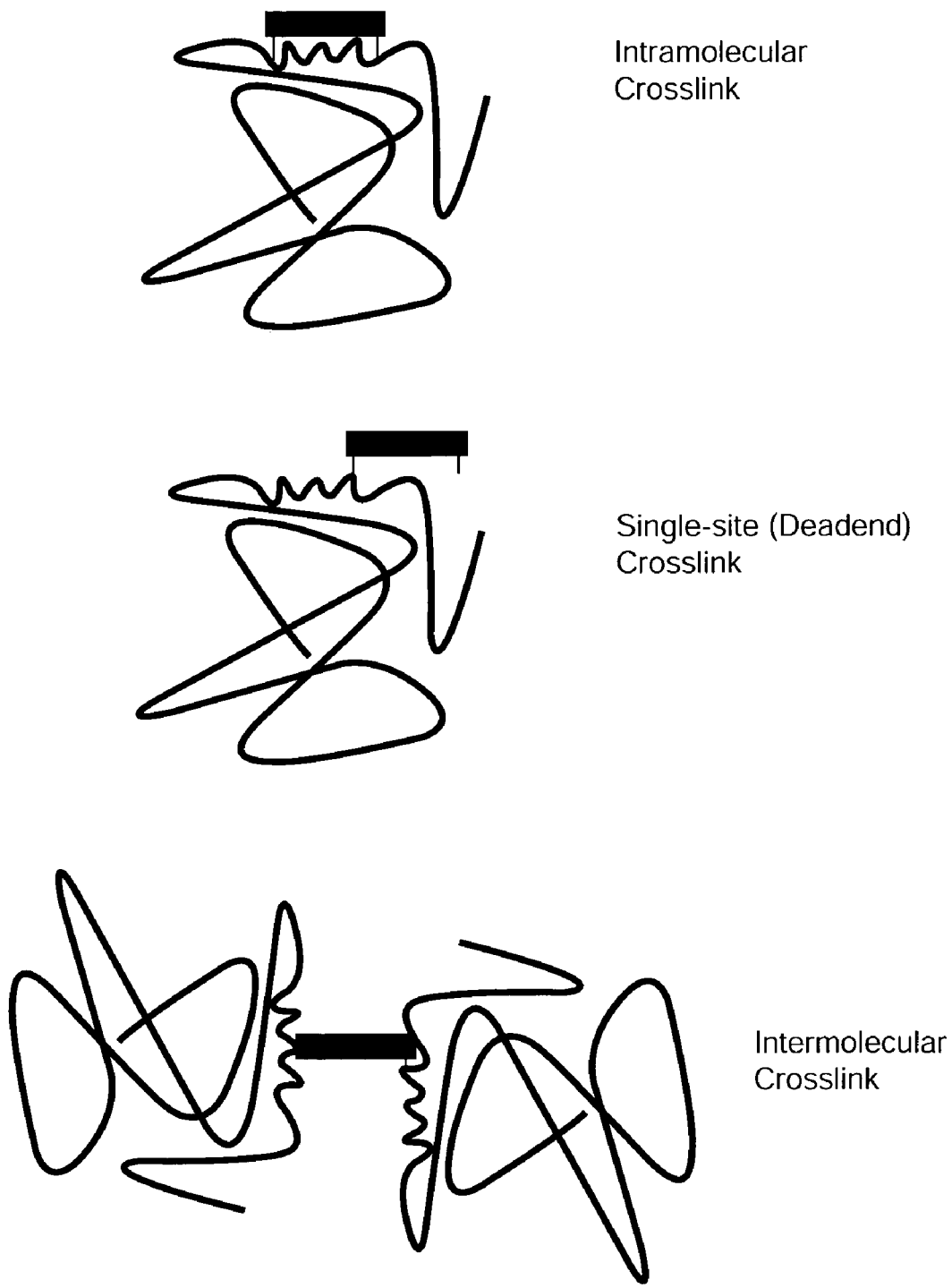
FIG. 5 illustrates the potential outcomes of the crosslinking reaction.

In either case, the resulting products will contain a mixture of proteins containing the following outcomes: 1) a crosslinker covalently attached to the protein at only one end (a dead-end crosslinker case, little useful information regarding distances), 2) a crosslink involving two spatially distinct sites attached to a single protein (protein monomer with two covalently linked sites, the desired outcome), and/or 3) a crosslinker joining two separate protein molecules (inter-protein crosslinking, generally not desired unless protein—protein interactions are being investigated). See FIG. 5.

Figure 6:
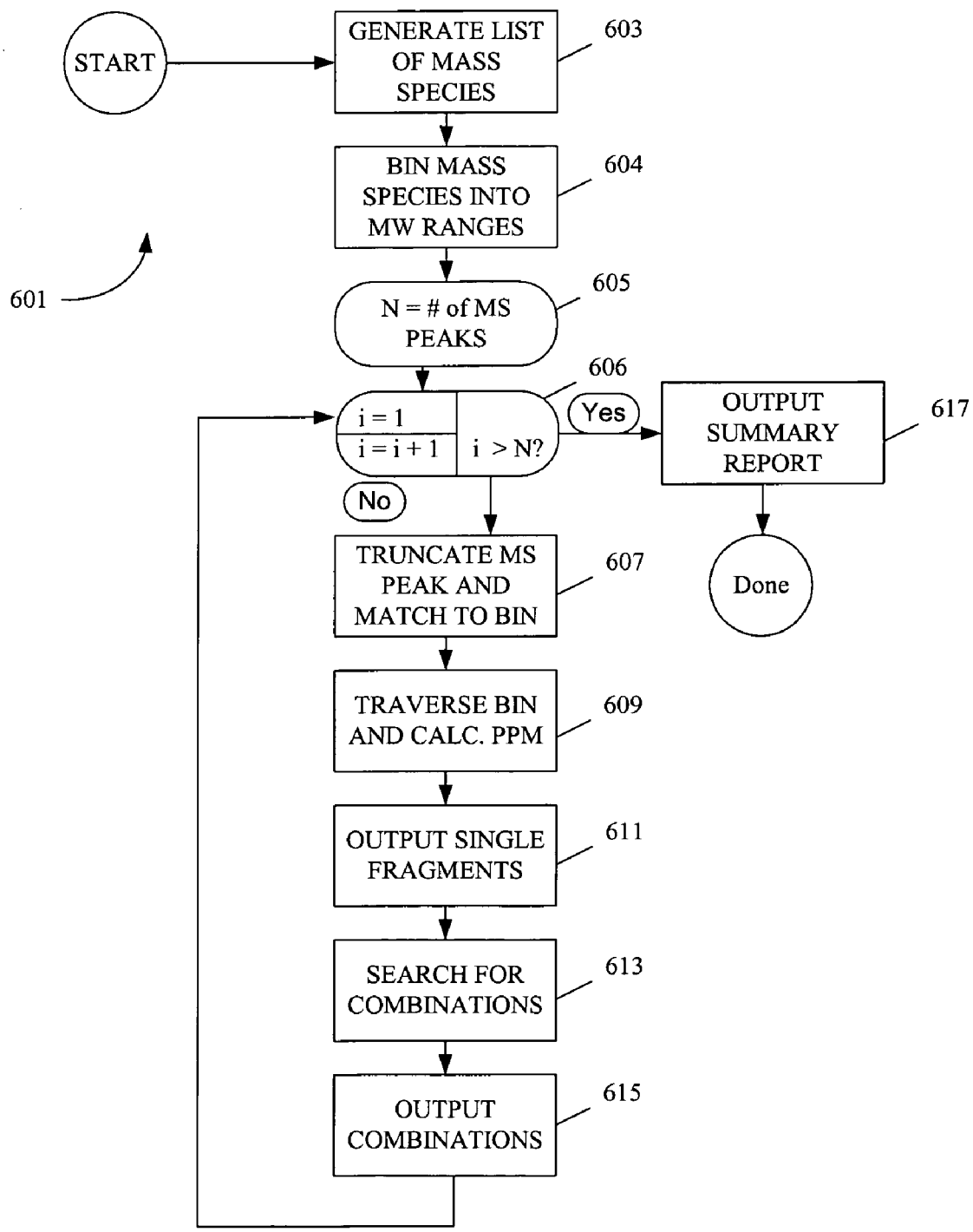
FIG. 6 is a flowchart illustrating a computational process for generating distance constraint information.

FIG. 6 describes one suitable computational process for generating distance constraint information. See 601. The process begins at 603, with the computational system generating many of the expected fragments, given the particular cross-linker(s) and protease(s) used on the protein. To generate this list, the system usually requires at least the following inputs: a primary sequence, identification of a protease, and identification of a cross-linking agent. For example, if the protein was treated with trypsin, which C-terminally cleaves lysine and arginine, then all the potential fragments generated from the primary sequence with these cleavage products are considered. In addition, some of the protein fragments will have the cross-linking agent attached to them, so these modified fragments may be listed as well. For instance, if the cross-linker BS3 is used (which bonds to lysine), then some additional potential fragments having lysine residues and bound BS3 may be listed with the mass of the cross-linker added. In a preferred embodiment, the list of expected fragments does not include many or any fragments that contain two or more peptide backbones linked by one or more cross-linking agent. Such species may be accounted for later in the process. In this embodiment, when fragments containing cross-linking agents are considered, the bound cross-linking agent will have one free (unbound) terminus. When considering a peptide fragment containing such cross-linking agent, various sub-species may be present depending upon the chemical state of the agent's terminus. For example, the same protein fragment may be listed with the following molecular weight variations: fragment with the entire linker attached (linker plus leaving group) and the fragment with hydrolyzed linker arm attached (usually hydrolyzed). If a particular fragment has two or more lysine groups, for example, then the possibility of intra-fragment cross-links between the lysine residues may be listed as well.

Figure 7:
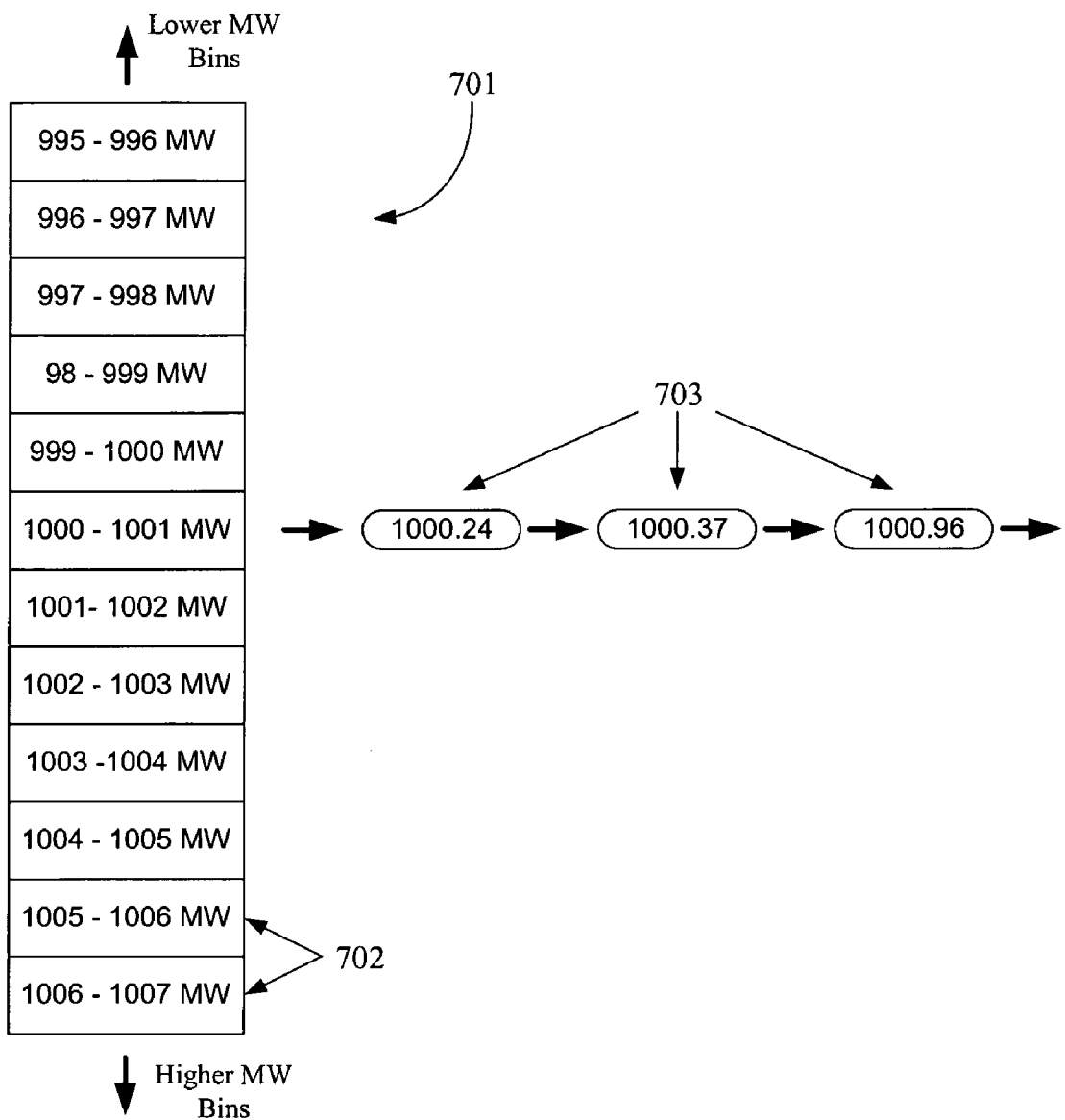
FIG. 7 is a schematic illustration of a binned list of calculated protein fragments as used in the flow-chart of FIG. 6.

As part of 603, the system calculates the mass of each of the generated fragments in the list. This allows the fragments to be correlated with the mass data from a mass spectrometer. Once all the fragments have been generated, they are organized by binning them into molecular weight ranges. See 604. FIG. 7, 701 is a schematic illustration of a binned list of calculated protein fragments, including several individual bins. See 702 for example. The individual mass species within a bin are represented as a linked list. See 703. The mass spectrometry data obtained from the actual proteolyzed protein can then be matched against the binned collection of expected species.

After the list of fragments and associated masses has been generated and binned as described, the actual mass spectrometry data may be analyzed. Preferably, the system considers each MS peak generated from an analysis of the proteolyzed protein. In process 601, this is represented as operations 605 and 606, where the system sets a variable N equal to the number of peaks to be considered (605) and iterates over those various peaks (606). Iterative loop operation 606 initially sets an index value "i" equal to 1. It then determines whether the current value of i is greater than the value of N. If not, it performs various operations to identify the chemical structure of the species that created the peak.

In a preferred embodiment, a control spectrum or spectra are subtracted from the MS data before the process of FIG. 6 is carried out. Because only the protein fragments with linked residues (even if the linked is attached to nothing at the other end) are generally of interest, it is helpful to subtract the MS data corresponding to the residues with cross-linker in this manner. In a preferred embodiment, the list of mass species can be partially built up using an already existing library of peptides, thus simplifying the task of generating the list.

Thus, assuming that the system is considering the first MS peak, the observed mass of that peak will be truncated and matched to its corresponding bin. See 607. The system will then traverse the list of mass species in that bin, and calculate a parts per million (PPM) error for each. See 609. The program will then output all the fragments that fall within a chosen allowable PPM range of the calculated mass species. See 611. Note that one input to the system may be a user-adjustable PPM error window.

The process has not yet accounted for mass species that correspond to fragment-to-fragment cross-links. In this embodiment, the program does not store all these combinations, but instead searches the list of individual protein fragments and determines if two fragments, linked together, match an observed MS peak. See 613. This process, in more detail, is as follows. The process will search for combinations for each MS peak in an iterative process much like steps 605 and 606. Since it can be assumed that there is a linker in the combination, the process will take the weight of the MS peak and subtract the linker weight. It will then go to the lowest occupied molecular weight bin. For each fragment in the bin, there is a check to determine if a fragment partner exists which can crosslink to the fragment and which has a mass, when added to the mass of the first fragment, sums to the corrected MS peak. This is repeated for all fragments in that bin, and for subsequent bins, until all the bins have been accounted for in the combination search. Inter-peptide cross-linked species meeting the PPM error window are output at 615. In a specific embodiment, the program does not search for combinations of three or more cross-linked fragments, as such fragments are only rarely generated.

After the peak at hand has been analyzed and the relevant matches output at 611 and/or 615, process control returns to iterative loop operation 606, where the value of i is incremented by 1. The system again determines whether the current value of i exceeds the value of N. Assuming that there are more peaks to consider, the next peak (i) is selected and process control returns to operations 607, 609, 611, 613, and 615, which are performed as described above, but with reference to the new peak (i).

After all the MS peaks have been considered (at which point i becomes greater than N), operation 606 is answered in the negative. At this point, process control is branches to 617, where the system outputs the final results. A typical readable output format, as shown in FIG. 8, lists the mass of the MS peak, the protein fragment or combination of fragments it corresponds to, the number of times the peak was observed over the series of MS scans, the PPM error, and the positions of cross-link attachment. Mass redundancies, that is, the MS peaks that are found to correspond to more than mass species, have been found to be fairly rare, particularly if an allowable PPM error of about 5 is chosen. These can be resolved after the computer program has output the final results. The results are used as distance constraint information to re-rank the candidate structures (see operation 207 of FIG. 2 and FIG. 13). The software has been written to accommodate other cross-linkers, in addition to BS3, and it should be understood that the software of this invention can work with other proteolytic and cross-linking reagents. It can be extended to handle embodiments where more than one cross-linker or protease has been used, and where multiple digests, each with different cross-linkers and proteases, has been carried out.

Figure 9:
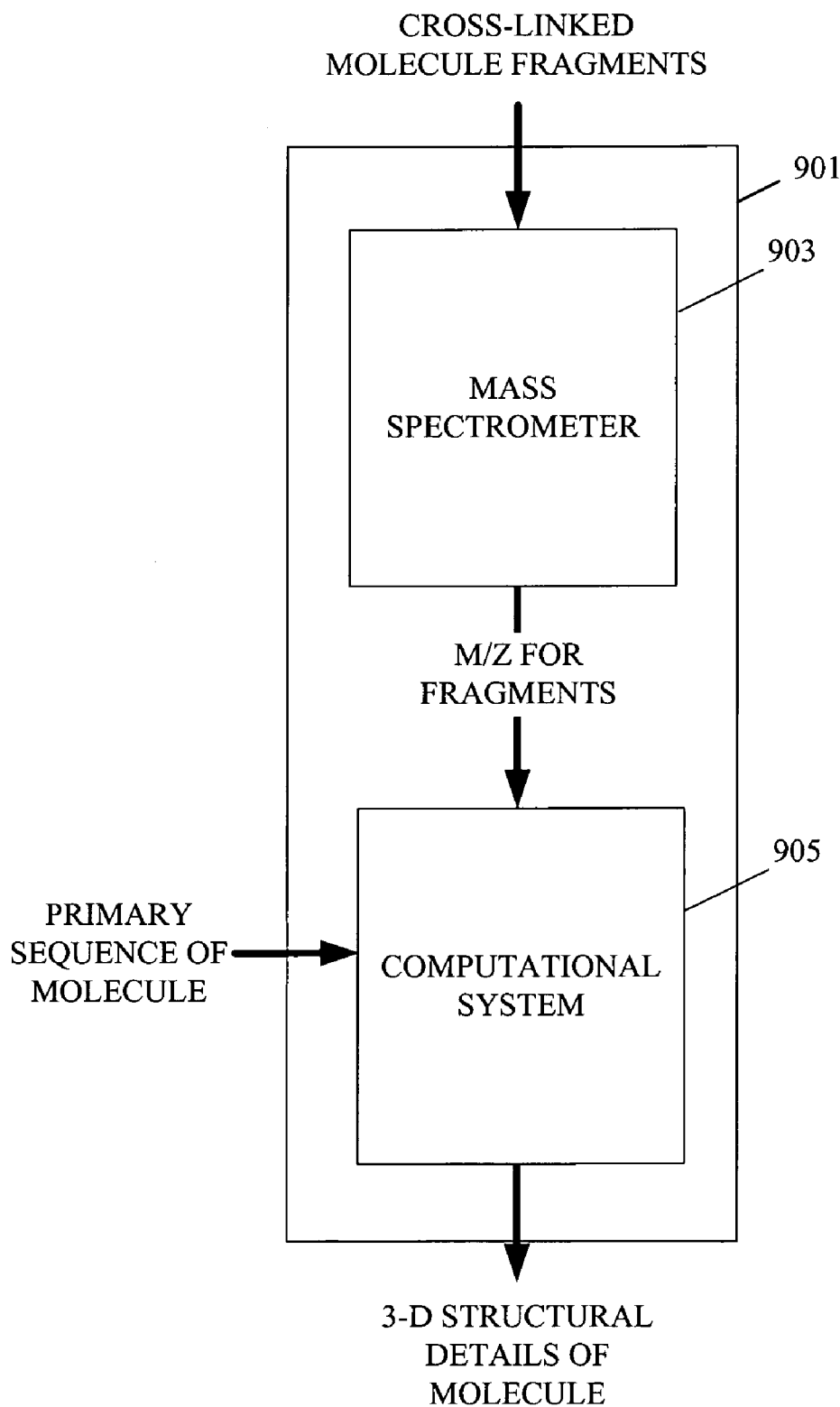
FIG. 9 is a schematic illustration of the mass spectrometer and computational system apparatus of the current invention.

An apparatus overview of this mass spectrometer and computational system is illustrated in FIG. 9, 901. Cross-linked molecule fragments are an input to the mass spectrometer 903, in this embodiment, protein fragments. The mass spectrometer outputs M/Z (mass over charge) for each fragment, which is fed into the computational system 905, along with the primary sequence of the molecule. The computational system then outputs 3-D structural details of the molecule.

Enrichment of two Site Intramolecular Crosslinks

Following crosslinking of the proteins, it is optional to enrich the reaction products for proteins having intramolecular crosslinks, and to minimize, and preferably eliminate, proteins having single site and/or intermolecular crosslinks. For example, intermolecular crosslinks are identified using size exclusion chromatography. Other methods may also be employed, as will be obvious to one skilled in the art upon reading this disclosure. Alternatively, the reaction conditions of the crosslinking reaction(s) can be chosen to provide reaction products having a degree of single site and/or intermolecular crosslinking sufficiently low that enrichment following the crosslinking reactions is unnecessary. After the reaction is complete, and any desired enrichment of the reaction products is performed, an initial mass spectrometric analysis of the protein products is optionally carried out to determine the overall reaction stoichiometry. The shift in mass of the unmodified protein (M) to modified protein (M') will give the average number of crosslinker modifications, since the expected mass of the crosslinker modification is known. Both the absolute and relative concentrations of the crosslinker and protein are important parameters in the experimental design. Ideally, one would like the average total number of covalent modifications of the protein made by the crosslinker to be fewer than one crosslink per protein (i.e., number of crosslinker modification/protein ◂1) to avoid significant perturbation of the protein tertiary structure that could generate false distance constraints). In addition, the crosslinking reaction can produce more single-site dead end modifications to the protein than the desired two-site intra-protein crosslinks. However, it is likely that simple single-site modifications have considerably smaller perturbation on the overall structure than a two-site crosslink.

In the case of a Lys—Lys specific crosslinker (e.g., BS3) one can distinguish these two outcomes if the mass spectrometer has a resolving power capable of resolving the mass difference between these two reaction possibilities, e.g., <0.1%. If the protein has a mass of 20,000, the mass of a singly labeled site (Lys-labeled) with the second end hydrolyzed by water, would be 20,156. This mass shift is 18 Da higher in mass than if a two-site reaction (Lys to Lys) has occurred with the protein. M=20,138.

Figure 10:
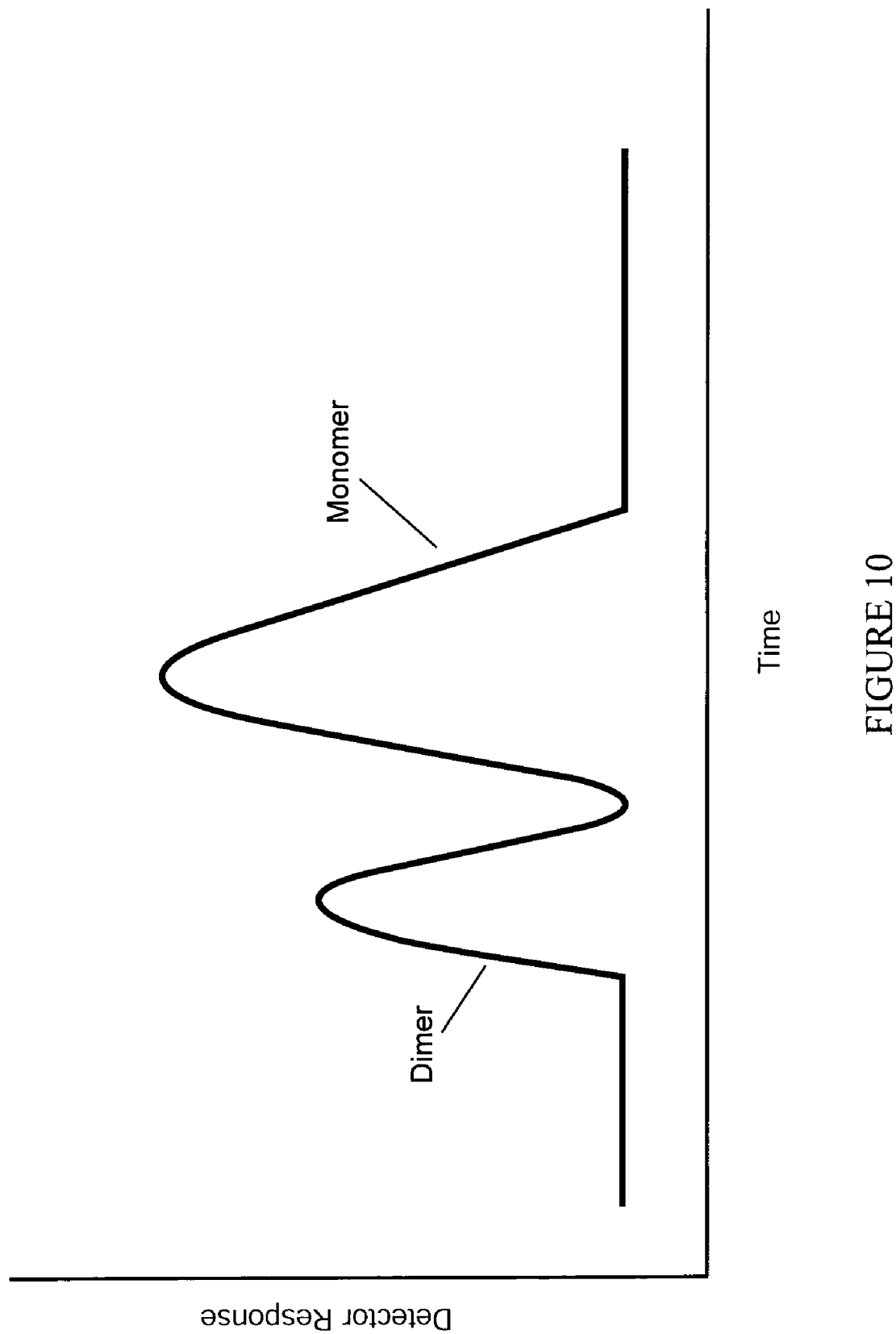
FIG. 10 is a line graph showing the difference between monomer and dimer crosslinked molecules in the elution of a size selection chromatography procedure.

Because the crosslinking agent can potentially form covalent bonds with amino acid residues of two (or more) different proteins, size-exclusion chromatography or other separation techniques can be employed (either under denaturing or non-denaturing conditions) to isolate intracrosslinked proteins from proteins having inter-protein crosslinks. For example, the crosslinked dimers can be removed using BioRad BIOSELECT™ columns. Under non-denaturing condition (100 mM $NH_4HCO_3$, pH 7.0) using BioRad BioSelect 125–5 columns (300×7.8 mm, each), two peaks are generally observed, an early eluting peak containing protein dimers and a later eluting peak containing monomers (FIG. 10).

The fraction containing the protein monomers can be further separated under denaturing conditions (8M urea, 100 mM citrate buffer, pH 5) using a TosoHaas G2000 column into two sub-components; an early eluting peak containing primarily protein monomer with dead-end or singly-labeled linkers (no actual crosslinks, just surface labeling) and a later eluting peak containing primarily monomers with actual intramolecular crosslinked amino acids.

Other size separation methodology can also be incorporated in this method, such as gel electrophoresis, filtration or dialysis. In the case of very small amount protein available, separating the dimer from monomer can be achieved by SDS PAGE. Then individual protein gel bands can be excised and the protein can be electro-eluted.

Fragmentation and Size Separation

Following crosslinking, the protein of interest is fragmented into peptides by digestion and the peptide products are subsequently separated, e.g., by reverse-phase chromatography (see FIG. 11). Proteolytic enzymes for fragmentation in the method of the invention possess the activity used to cleave the crosslinked protein into smaller, more manageable pieces. This may be any enzyme or chemical activity known in the art which is capable of repeatedly and accurately cleaving a protein at particular cleavage sites during digestion. Suitable activities are widely known and a suitable activity may be selected using conventional practices.

Examples of such enzyme or chemical activities would include, as representative examples: the enzyme trypsin which hydrolyzes peptide bonds on the carboxyl side of lysine and arginine; the enzyme chymotrypsin which hydrolyzes peptide bonds on the carboxyl side of aromatic residues (phenylalanine, tyrosine, and tryptophan); cyanogen bromide (CNBr) which chemically cleaves proteins at methionine residues; endoproteinase Glu-C which hydrolyzes highly specifically peptide bonds at the carboxylic side of Glu (in ammonium bicarbonate, pH 7.8 or ammonium acetate buffer, pH 4.0) or Glu and Asp (in phosphate buffer, pH7.8); and endoproteinase Asp-N, which hydrolyzes peptide bonds at the amino side of Asp and Cysteic acid. Less specific proteases can also be used in order to obtain manageable peptides, such as: Thermolysin, which hydrolyzes peptide bonds involving the amino group of hydrophobic amino acids with bulky side chains like Leu, Ile, Met, Phe, Trp and Val; and pepsin, which cleaves proteins preferentially at peptide bonds involving the carboxylic groups of aromatic amino acids and other hydrophobic amino acids (Phe and Leu). The enzyme trypsin is often a preferred enzyme activity for cleaving proteins into smaller, more manageable pieces because trypsin is characterized by low cost and highly reproducible and accurate cleavage sites at the amino acids arginine and lysine occurring in the amino acid sequence of protein molecules. Typical reactions conditions used to generate the final peptide mixtures from the labeled protein using trypsin are 50 mM $NH_4HCO_3$, pH 9, 20:1 weight ratio of trypsin to protein, and a 2 hour incubation at 37° C.

A combination of the proteases and chemical reagents can also be applied to the crosslinked proteins to generate a peptide mixture. In the case of following size-separation by SDS PAGE, in-gel digest of protein by proteases can be used and the resulting peptides can be extracted from the gel slice. The resulting peptide mixture will contain unlabeled and labeled peptides, where the labeled fraction is further divided into intermolecular, intramolecular or singly labeled crosslinks.

Following digestion, the fragments can be fractioned using any methodology known to one skilled in the art. Preferably, the peptides are fractioned using a chromatographic column. The chromatographic column includes a chromatographic medium which, in cooperation with a suitable solvent system, is capable of chromatographically fractionating peptide digests following the digestion reaction. The chromatographic column includes an inlet port for receiving the peptide digests and an exit port for discharging an effluent comprising the chromatographically fractionated peptide digests.

In a preferred embodiment, the chromatographic column is a reverse-phase HPLC analytical column comprising a fractionating medium capable of fractionating the peptide digests when the digests are eluted through chromatographic column using reverse phase HPLC techniques. In order to practice such techniques, it is preferred that the chromatographic medium is hydrophobic because the peptide digests themselves tend to by hydrophobic in nature. An exemplary HPLC analytical column suitable for use in the practice of the present invention is commercially available as the Vydac TM C-18 HPLC column from the Separations Group, Inc., of Hesperia, Calif.

Identification of Peptide Fragments

After the crosslinked proteins have been fragmented and optionally purified, the peptide fragments are then identified in order to assign crosslinks to specific peptide fragments within the protein structure. This may be done using various techniques, including Edman sequencing, chromatography, mass spectrometry, or a combination of these methods. Grant et al., *Methods Enzymol.* 1997 289:395–419.

One method of the identification of the crosslinked peptides will involve either on-line chromatography-mass spectrometry or off-line chromatography followed by mass spectrometry. The chromatography component consists of reversed-phase separation using C4, C8, C18 or similar separation schemes. A gradient elution profile starting from 100% aqueous to 70–100% organic (e.g., acetonitrile or methanol) is employed and peptides are either collected in fractions off-line or eluted directly into the source of an appropriately configured mass spectrometer. A typical gradient for a C18 or C8 column would be a linear gradient starting with 100% solvent A to 100% solvent B in 70 minutes (where solvent A=$H_2O$ with 0.1% trifluoroacetic acid (TFA) and solvent B=70% acetonitrile/30% $H_2O$ with 0.8% TFA). In the case where TFA is undesirable for the mass spectrometer, formic acid can be used instead of TFA.

For off-line HPLC separation, an Eldex MicroPro HPLC can be used, and preferably is fitted with a Michrom MAGIC MS reverse-phase column (0.2×5 0 mm) operating at 1 μl/min. Alternatively, an LC Packing Fusica II reverse-phase column (0.3×150 mm, 5 mL/min) with a higher loading capacity can be used, depending on the amount of material one has and degree of peptide separation desired. In either case, a gradient program where A=0–1% TFA/water and B=0.08% TFA in 70% acetonitrile will range from 10% solution B/90% solution A to 90% solution B/10% solution A in 60 min. The peptides will be detected at 210 nm with an ABI 785A UV detector fitted with a LC Packings capillary Z-cell and either collected into Eppendorf tubes or directly onto plates for subsequent MS analysis.

There are several MS instruments that are suitable for the detection of the crosslinked peptides, including but not limited to 1) matrix-assisted laser desorption ionization (MALDI) time-of-flight (TOF) instruments where individual HPLC fractions were first separated off-line, 2) an electrospray ionization (ESI) orthogonal-TOF mass spectrometer with on-line HPLC and/or a 3) ESI ion-trap instrument, also with on-line HPLC detection. Still other methods will be obvious to one skilled in the art upon reading the present disclosure.

There are several important considerations in this mass determination, including the overall mass accuracy, dynamic range of detection, and mass range. In general, a mass accuracy of better than 100 ppm is desired such that one is able to limit the possible interpretations as to the crosslinked peptide identity. In practice, mass accuracies of up to or better than 10 ppm can be achieved on many MS instruments with proper internal calibration. This is highly desirable, as one can more readily assign peptide (and peptide crosslinks) based on this higher level of mass accuracy. A tandem MS experiment, can be carried out on selected peptide ions to provide additional fragmentation data ("sequence tags") which is in turn used to confirm peptide identity and/or assign the precise amino acid positions involved in the crosslink.

One embodiment of the present invention preferably employs the use of time-of-flight (TOF) mass spectrometry instruments to determine the identity of cross-linked peptides. TOF mass spectrometry separates ions according to their mass-to-charge (m/z) ratio by measuring the time it takes generated ions to travel to a detector. TOF mass spectrometers are advantageous in the present invention because they are relatively simple, inexpensive instruments with virtually unlimited mass-to-charge ratio range. TOF mass spectrometers have potentially higher sensitivity than scanning instruments because they can record all the ions generated from each ionization event. TOF mass spectrometers are particularly useful for measuring the mass-to-charge ratio of large organic molecules where conventional magnetic field mass spectrometers lack sensitivity. Exemplary TOF mass spectrometers that may be used in the present invention are shown in U.S. Pat. Nos. 5,045,694, 5,160,840, and 5,627,369 specifically incorporated by reference herein.

The performance of a mass spectrometer is only partially defined by the mass resolution. Other important attributes are mass accuracy, sensitivity, signal-to-noise ratio, and dynamic range. The relative importance of the various factors defining overall performance depends primarily on the type of sample, but generally several parameters must be specified and simultaneously optimized to obtain satisfactory performance for a particular application. These parameters may be varied for optimal resolution in the method of the invention, which would be obvious to one skilled in the art upon reading the present disclosure.

MALDI Mass Spectrometry

Matrix-assisted laser desorption/ionization (MALDI) is particularly advantageous in biological applications, and thus for use in the methods of the invention, since it facilitates desorption and ionization of large biomolecules in excess of 100,000 Da molecular mass while keeping them intact. Thus, in one preferred embodiment, the MALDI mass spectrometry technique is used. In MALDI, the ions generally have a substantial average velocity after leaving the surface, which is the same to a large extent for ions of all masses, and a large spread around the average velocity. The average velocity leads to a non-linear relationship between the flight time and root of the mass. The spread leads to a low mass resolution and when measuring the signals of individual ion masses, however there are methods which improve mass resolution. The relationship for conversion of flight time into mass is called "mass scale" here for the sake of simplicity.

Other modifications of MALDI mass spectrometry have also been reported, and optionally can be used in the methods of the present invention. Researchers reported improved resolution as well as fast fragmentation of small proteins in Lennon et. al., *Proceedings of the 42nd ASMS Conference on Mass Spectrometry and Allied Topics*, May 29–Jun. 3, 1994, Chicago, Ill., p. 501. Also, researchers reported significant resolution enhancement when measuring smaller synthetic polymers on a compact MALDI instrument with pulsed ion extraction in Breuker et al., *13th International Mass Spectrometry Conference*, Aug. 29–Sep. 3, 1994, Budapest, Hungary. In addition, researchers reported considerably improved mass resolution on small proteins with a pulsed ion extraction MALDI source in Reilly et al., *Rapid Commun.*, Mass Spectrometry, 8, 1994, 865–868 and Colby, Rapid Commun. *Mass Spectrom.*, 8, 1994, 865–868.

Ion reflectors (also called ion mirrors and reflectrons) can be used to compensate for the effects of the initial kinetic energy distribution. An ion reflector is positioned at the end of the free-flight region. An ion reflector consists of one or more homogeneous, retarding, electrostatic fields. As the ions penetrate the reflector, with respect to the electrostatic fields, they are decelerated until the velocity component in the direction of the field becomes zero. Then, the ions reverse direction and are accelerated back through the reflector. The ions exit the reflector with energies identical to their incoming energy but with velocities in the opposite direction. Ions with larger energies penetrate the reflector more deeply and consequently will remain in the ion reflector for a longer time. In a properly designed reflector, the potentials are selected to modify the flight paths of the ions such that ions of like mass and charge arrive at the detector at the same time regardless of their initial energy. Those skilled in the art will recognize such modifications and their application to the methods of the present invention upon reading this disclosure, and thus these modifications and principles may be applied to the disclosed technology as well.

Electrospray Ionization Mass Spectrometry For higher mass accuracy (≦20–50 ppm) and on-line HPLC/MS analysis, so-called "electrospray ionization" (ESI) mass spectrometry is used in the methods of the invention. In electrospray ionization, an electric potential is applied to a liquid containing the analyte(s), usually via a conductive capillary needle. An analyte in solution is sprayed from a conducting needle with approximately a 75–100 μm inner diameter, at a high voltage, e.g., 3000V, towards a conducting aperture plate at a potential between ground and about 300 V leading to the input of the mass spectrometer. Alternatively, a high voltage of the same magnitude but opposite polarity may be applied to the entrance aperture of the mass spectrometer. Ions are produced in the high electric field, and are then analyzed in a mass spectrometer.

ESI can convert analytes in solution, at ambient temperature and pressure, directly into gas-phase ions without excessive fragmentation. ESI mass spectrometry is suitable for the analysis of nonvolatile compounds that are either polar or ionic. An advantage of ESI over other soft-ionization techniques such as fast atom bombardment or thermospray is the formation of multiply charged species, making ESI well suited for the analysis of high molecular weight (up to 1,000,000 Da) biomolecules and polymers. See Fenn et al., "Electrospray Ionization-Principle and Practice," *Mass Spectrom. Rev.*, vol. 9, pp. 37–70 (1990). For general background on the mechanisms of electrospray, see P. Kebarle et al., *Anal. Chem.* 65: 972A–986A (1993).

For this embodiment, ESI-TOF is preferably carried out using a Mariner ESI-TOF mass spectrometer coupled to an Applied Biosystems 140B syringe pump HPLC system fitted with a capillary HPLC column (Fusica 200–300 μI.D. by 10–15 cm; C18 or C4 Packings). A gradient solvent consisting of 0.1% formic acid in H20 (solvent A) and 0.05% formic acid in 5/2 (v/v) of ethanol/propanol (solvent B) will be employed starting from 10%–60% B in 70 min.

Structural Modeling

Figure 12:
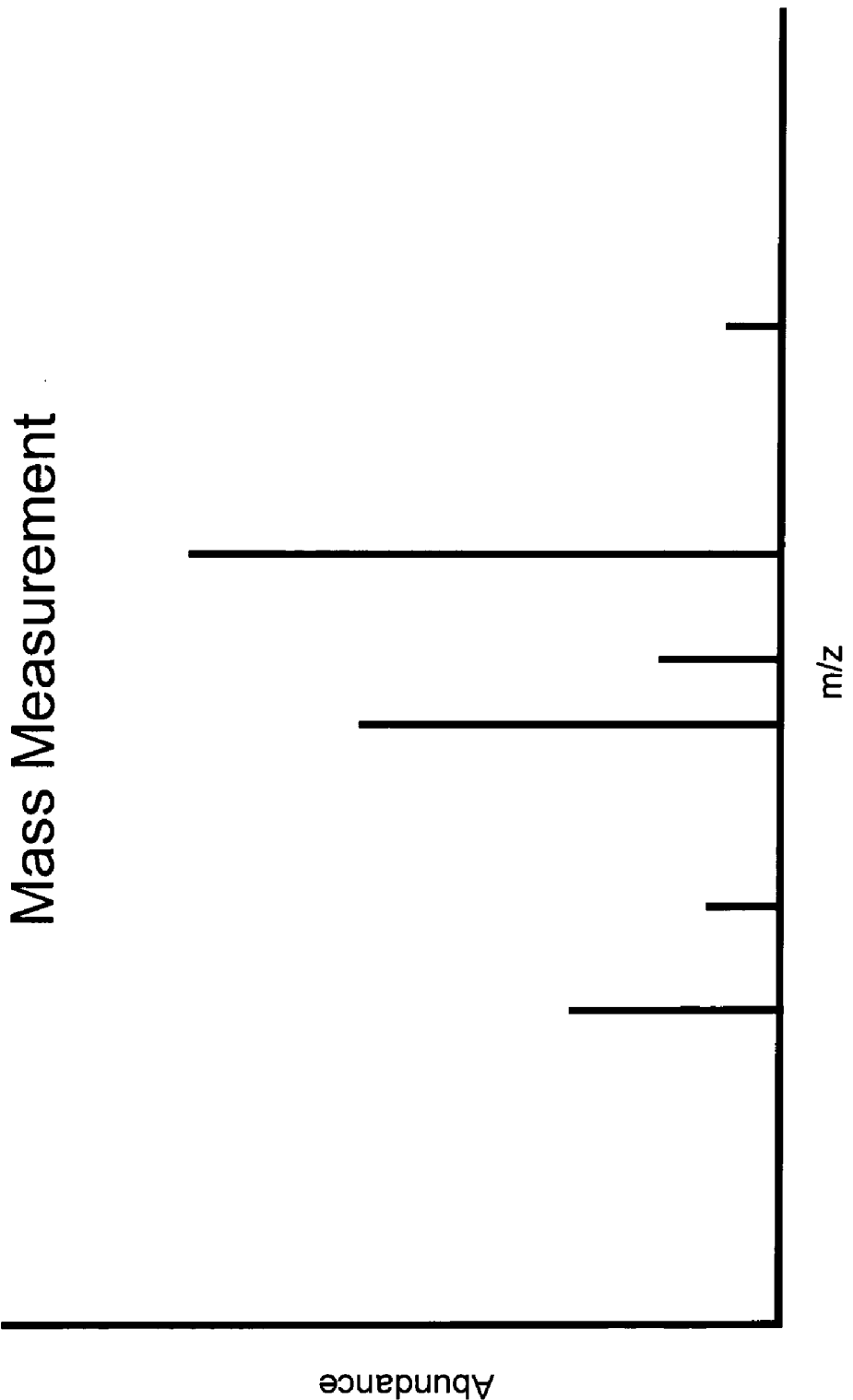
FIG. 12 is an illustration of mass spectrometric analysis of the peptide fragments present following proteolysis of the crosslinked protein.

The computational strategy used for structural modeling utilizes all experimental distance constraints between target amino acid pairs from the experimental peptide fragment data for the determination of fold-family, domain—domain geometries, and/or tertiary structures using a variety of computational approaches. In the limit of many constraints, structures could be generated directly using distance crosslinks. The same techniques can also be used to orient domains within a full-length structure, to determine the interactions between monomers within an oligomer, or to define a receptor-ligand complex. The combination of such analysis will generate a structural model of the tertiary structure of the protein. See FIG. 12. Such analysis is preferably performed with the aid of spatial geometry software.

Structural modeling can be extended to the study of uncrosslinked, modified, or crosslinked nucleic acid sequences, peptide or peptoid sequences with unusual amino acids, oligosaccharides, or any other polymer of defined sequence. Preferably, the software can incorporate various different chemical or photochemical crosslinkers with known chemical end products, including data from: monovalent (affinity labeled) reagents, homobivalent crosslinkers, heterobivalent crosslinkers, and crosslinkers with a valency greater than 2.

Once a set of structural models have been generated for a sequence of interest, they can be evaluated based on their compatibility with the experimentally-derived distance constraints and/or based on their computed physical properties. A model's compatibility with constraints is a function of the constraint errors associated with the model and the number of constraints defined by the model, e.g those constraints linking residues in regions defined by the alignment, x-ray crystallography, or NMR. Assessing a model based on its physical properties can involve: calculating the distribution of hydrophobic/hydrophilic amino acids; mapping its hydrogen-bond network; locating disulfide bridges; functional mapping of mutagenesis data; assessing the complementarity of the model's secondary structure and the secondary structures predicted for the sequence; insuring that critical electrostatic interactions are preserved; identifying sites of van der Waals clashes; evaluating the sequence-structure-sequence similarity, or any combination of the above.

Even with few generated crosslinks (about 10% of the number of amino acid residues) it is possible to determine the fold-family for a sequence of unknown structure. The critical theoretical leap for fold recognition involves a focused analysis of the space of all possible protein structures. The structural evaluations are limited to those structures in the space that are likely candidate structures for a sequence of interest.

Fold-family determination could therefore optionally include the generation of hypothetical structural models by threading the sequence of interest through a library of representative protein structures followed by the evaluation of models via the application of distance constraints obtained from the crosslinking data set. If a model is found with a low constraint violation, this model is considered to be a good candidate for further homology modeling studies. The first step in the analysis is the generation of a set of structural models for a sequence of interest. Structural models can be generated by threading a set of known protein structures and calculating de novo structures using either distance geometry or ab initio methods such as constrained energy minimization or molecular dynamics. Structural models can also be generated by using secondary structure prediction methods, motifs in the sequence, homology modeling, or a combination of these and other techniques as apparent to one skilled in the art upon reading this disclosure.

Distance geometry programs are of particular use in the methods of the present invention. Distance geometry is a general method for converting a set of (N×N)-N distance bounds into a set of 3×N Cartesian coordinates consistent with these bounds. One such distance geometry program, DGEOM, is a distance geometry program for molecular model-building and conformational analysis available from Chiron Corporation of Emeryville, Calif. Havel, et al. *J Theor Biol.* 104:359–81 (1983); Havel et al. *J Theor Biol.* 104:383–400 (1983). Molecular structures can be described by the set of all pairs of interatomic distances produced using physical constraint and fragment identification. Using distance geometry programs such as DGEOM, moderate resolution structures can be produced using far fewer physical constraints than was previously predicted.

Any of the many methods of model generation can be applied at this step in the over-all methodology. The alignment methods described here are merely exemplary, and other methods may be used to deduce structures that are consistent with distance constraints. Two strategies that are particularly useful in the methods of the present invention are constrained threading and constrained sequence/structure alignment. Other possible methods include dynamic programming and clique detection.

The first step in the constrained threading procedure is to generate a set of structural models by threading a sequence through a database of sequence-unique protein folds. Various software programs are available in the art to generate such structural models. For example, the specific program we used to generate these models for FGF-2 (FGF2-BOVIN) is the public-domain software 123D. Alexandrov et al. "Fast Protein Fold Recognition via Sequence to Structure Alignment and Contact Capacity Potentials." *Protein Science Bulletin.* (1996). This program involves entering the sequence of the protein, determining the alignment mode and allowing the software algorithm to generate the model. In global alignments all positions are considered. In free shift alignments gaps at the beginning or at the end are not scored. Local alignments are maximal common substring alignments. For any of these alignment modes, the program will provide a given number of top scoring alignments. A version of this program can be accessed on-line at the http site cartan.gmd.de. Structural models considered by 123D to be the most complementary to the protein sequence, e.g., FGF-2 sequence, are then passed to the next step in our methodology, the model evaluation step. The top 20 threading models can be further examined for their compatibility with the experimentally-derived constraints using the equation:

$$E_t = \sum_{j=0}^{j<=i} 0 \text{ if } d_j <= d_o, d_j - d_o \text{ if } d_j > d_o$$

$E_t$ is the total constraint error, i is the number of distance constraints, $d_o$ is the pairwise distance separation, and $d_f$ is the pairwise distance defined by the structure for the two residues in constraint j. Thus $d_j$ is the distance observed in the candidate threading model. If $d_j$ is less than or equal to the distance $d_o$ defined by the length of the linker arm, then there is no constraint error contributed by that constraint j. If $d_j$ is greater than $d_o$, then the constraint error is defined by the difference between these distances. These functional forms for the constraint error calculation are exemplary, and other scoring functions may also be used as will be apparent to one skilled in the art upon reading this disclosure.

Only sequence-structure models with 50% of the pairwise constraints are generally evaluated to avoid considering models with artificially low constraint errors. The top 20 threading models are then ranked in order of increasing constraint error. For the constrained threading approach, the physical property evaluation is performed as part of the model generation stop. For example, the 123D threading potential includes terms for the sequence-structure similarity. The model evaluation step in this approach focuses on measuring the complementarity of each model to the experimentally-derived constraints.

Figure 13:
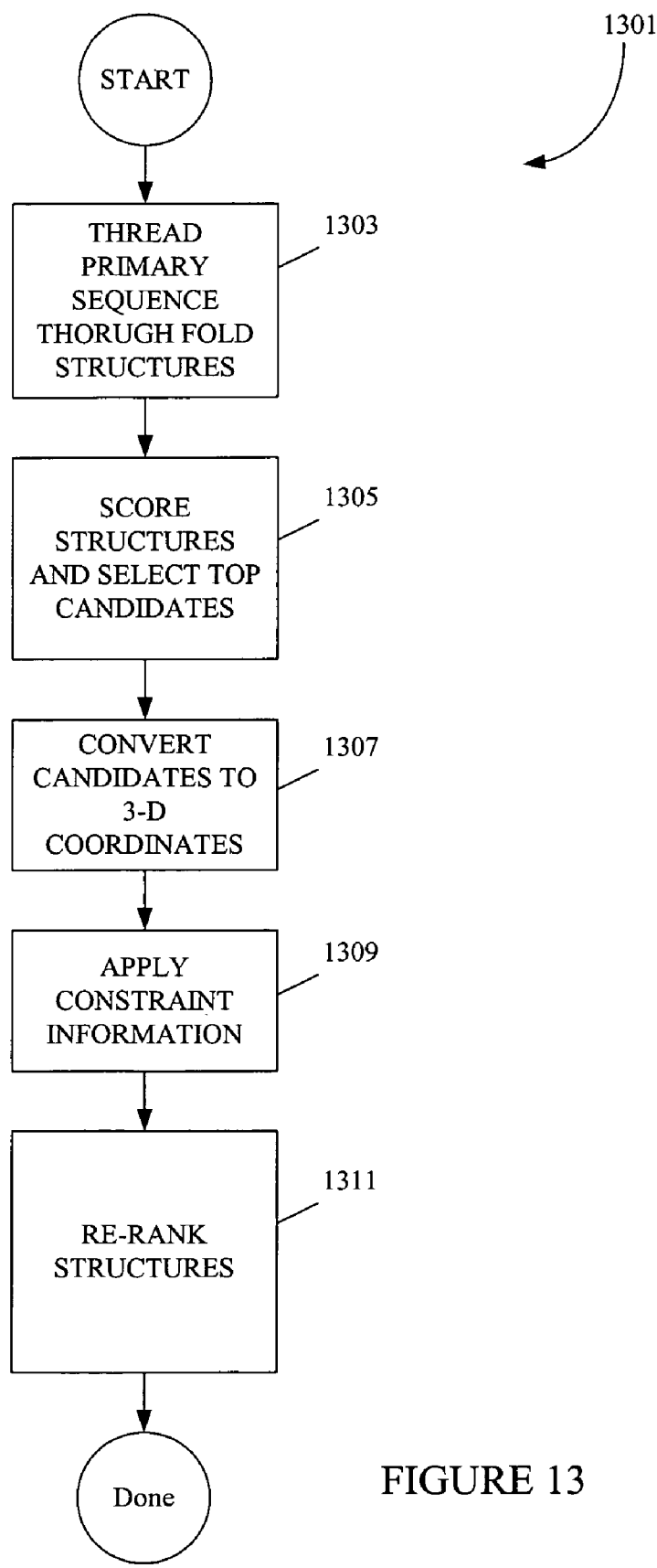
FIG. 13 is a flow-chart illustrates the computational threading process for generating and ranking structures.

An example of a constrained threading process is illustrated in more detail in the flowchart 1301 of FIG. 13. A set of protein structures having known 3-D conformations and fold or domain information is selected from a database such as Brookhaven Protein Databank. Information pertaining to each selected protein includes its primary sequence, as well as its secondary structure and the 3-D position of each residue. The primary sequence of the protein being analyzed is then threaded through each selected protein structure. See 1303. In other words, the backbone of the protein under consideration is laid on top of a backbone for the currently selected protein. After the protein under consideration has been aligned with a selected protein, the selected protein is scored. See 1305. If the public domain software 123D is being used, for example, it creates a score based on (1) sequence identity between the two proteins, (2) alignment of secondary structures between the two proteins, and (3) a contact capacity potential of the protein in its threaded format. The second scoring criterion involves approximating secondary structures of the protein based on the primary sequence. The third scoring criterion is based on the how closely the local environment (neighboring amino acids) of an amino acid residue matches with its empirically-determined preferred environment. Other software programs and other scoring criteria (e.g., hydrophobicity, potential mean force) can be used. In a typical embodiment, the top twenty candidate structures are then used in the next step of the computational process.

At 1307, the top candidates have their residues converted into 3-D coordinates by a computer program such as DGEOM, available from Chiron Corporation of Emeryville, Calif. The distance constraint information is applied to each candidate structure according to the formula listed above. See 1309. The candidate structures are then re-ranked according to their fit to the formula. See 1311.

Constrained Sequence/Structure Alignment

An alternative approach that can be used to investigate the information content of the list of restraints is constrained sequence/structure alignment. The "constrained sequence/structure alignment" approach employs the constraints to build a set of structural models, and the model evaluation stage consists of applying a pairwise hydrophobic contact potential to each model, and rank-ordering models based on this potential function. Bryant et al. "An Empirical Energy Function for Threading Protein Sequence Through the Folding Motif," *Proteins.* 1993 16 92–112. In this approach, alignments to the fold are defined by systematically matching residues of the target protein linked by a restraint to residues of the fold for which the interatomic distance of the alpha carbons is less than the extended crosslinker plus side chain atoms (<23.85 Angstroms in the case of the BS3 linkers).

The protein sequence can then be mapped onto the fold working back from the first-matched residue to the first residue of the sequence, or to the first of the fold, forward from-the first matched residue and back from the second in a symmetrical fashion, and forward from the second matched residue. For example, more than 115 of the 146 residues of FGF-2 have been determined with one insertion/deletion and 2 Angstroms average error over the full list of restraints associated with the mapped residues. Alignments can be scored using the pairwise hydrophobic contact potential defined by Bryant et al., 1993, and the best score obtained for each fold was retained to rank the fold.

The alternative embodiment of constrained sequencing/structure alignment will now be illustrated in more detail in the flowchart. The steps of this embodiment are slightly different than those describe in FIG. 13, but this embodiment fits in with the general approach outline in FIG. 2. In this embodiment, distance constraints are generated in the same manner as the above embodiment, using MS data. See 203 of FIG. 2 and all of FIG. 5. These distance constraints are applied to the primary sequence of the protein as it is threaded through the Brookhaven protein folds to yield candidate structures. See 205. The candidate structures are then scored and re-ranked using appropriate scoring functions. In a specific embodiment, the scoring functions of Bryant et al., 1993, are used, including contact capacity potential. The scoring functions used in this embodiment are described in that paper. Homology modeling is then carried out as described below. See FIGS. 14A and 14B and 207.

Figure 14A:
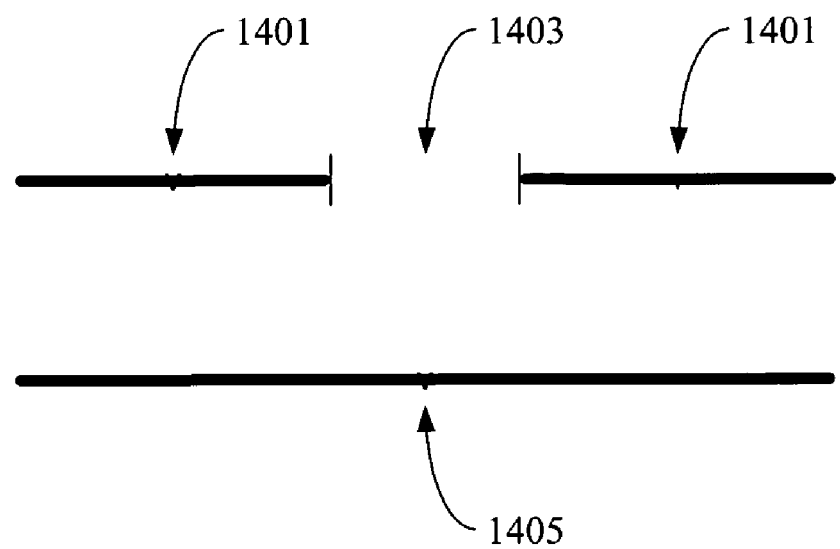
FIG. 14A is a schematic illustration of a protein structure with a gap that must be accounted for with homology modeling.
Figure 14B:
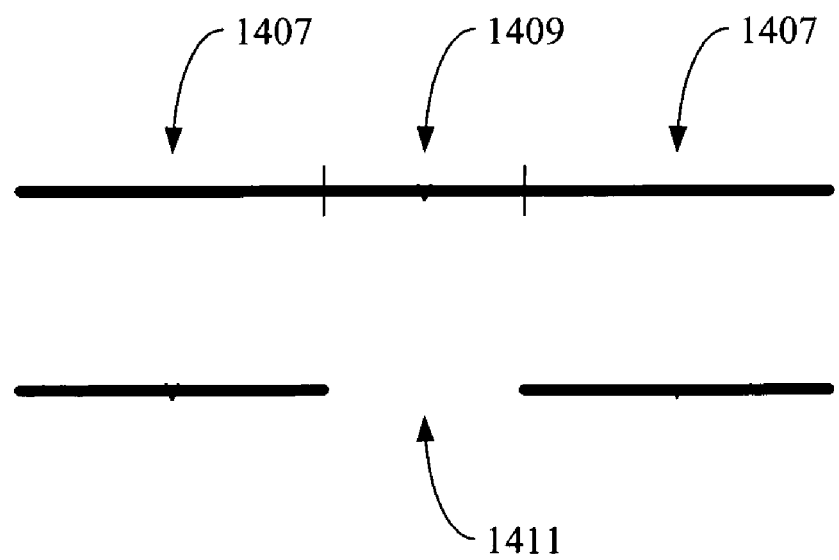
FIG. 14B is a schematic illustration of a protein structure with extra amino acid residues that must be accounted for homology modeling.
Figure 15:
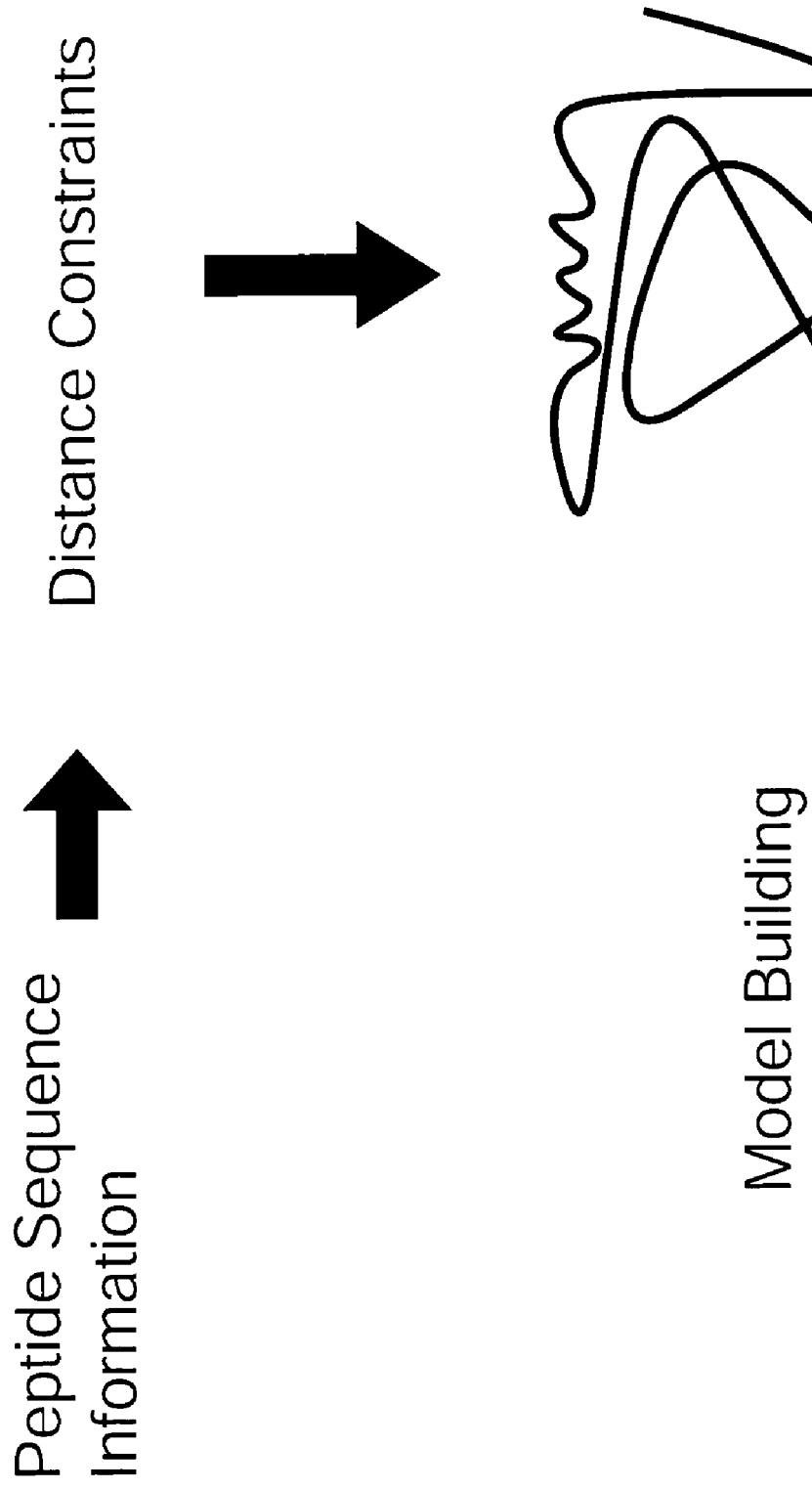
FIG. 15 is a schematic diagram of the steps for integrating information in order to model the three-dimensional protein structure.

After re-ranking, the top ranked structure or structures are then subjected to homology modeling to generate the full 3-D tertiary structure of the protein. First, discrepancies in the secondary structure of the protein (which is derived from its primary structure) must be reconciled with that of the Brookhaven protein that serves as the basis for the structure being modeled. One example of this is shown in FIG. 14A. FIG. 14A illustrates the protein being analyzed 1401, with a "gap" in its sequence 1403, as compared to the Brookhaven fold, 1405. Homology modeling software brings together the residues surrounding this gap in a manner that maintains the lowest energy configuration of the protein. Conversely, as shown in FIG. 14B, if the protein 1407, has extra residues 1409, as compared to the Brookhaven protein 1411, then the software can generate a loop that also maintains the lowest energy confirmation. Homology modeling software also will change the orientation of the residues and subgroups so as to minimize the energy conformation of the structure. Examples of homology modeling software that are used with the present invention are Sybyl, from Tripos, Inc. of St. Louis, Mo., and Midas, from the Computer Graphics Laboratory of the University of California, San Francisco of San Francisco, Calif.

Homology Modeling

In both model generation approaches, the model most complementary to the experimental constraints will be selected as a starting point for the construction of a homology model. The threading alignment can be used to match amino acids in the sequence to positions in the structure. Other alignment protocols could be used as well. The model can then be constructed using standard homology modeling techniques. Additionally, distance constraint violations within the model may assist in further refinement of the model. Refinement of the model could be done using distance geometry, energy minimization, and/or molecular dynamics.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The methods of the invention as described below were found to produce a moderate resolution structure (2–5 Å) structure using far fewer physical constraint distances than had been predicted in the art, generally about 10% of the number of amino acid residues in the protein. This unexpected and surprising result allows the methods of the invention to produce better resolution structures than would have been otherwise predicted. In addition, reasonable structures may be produced in a shorter amount of time than was predicted.

Example 1

Validation Experiments

The number and types of pairwise distance constraints required to construct the three-dimensional structure of a protein of interest was predicted prior to performing the intermolecular crosslinking technique. Seven different constraint types were applied to the calculation of the structures of 5 proteins using distance geometry: BPTI, alpha bungarotoxin, parvalbumin alpha, cyclophilin A, FGF-2. For each protein, an ensemble of 10 structures consistent with the constraints was generated.

The structures generated using exact interresidue crystallographic distances were of higher quality than those calculated from inexact distances. The best quality structures, as measured by RMSD from the crystal structure, were those calculated using polar polar amino acid crystallographic distances, secondary structure-derived constraints, and disulfide bond information. The structure of BPTI in particular was readily calculable with an RMSD of 2.72 Å due to the tight constraints imposed by its three disulfide bridges. Conversely, the cyclophlin A mixture proved to be the most challenging, as it lacks disulfide bonds and is the largest protein in the set (165 residues).

Addition of constraints based on secondary structure information generally lowered the RMSD, although the effects were most dramatic for parvalbumin and BPTI, which are 100% and 28% α-helical, respectively. The other proteins in the set, cyclophilin A, FGF-2, and α-bungarotoxin are classified by SCOP as all beta structures. Murzin et al. "SCOP: a Structural Classification of Proteins Database for the Investigation of Sequences and Structures." *J Mol. Biol.* 1995 Apr. 7;247(4):536–40. The secondary structure constraints lower the final RMSD in helical systems because more constraints are required to accurately define the structure of an α-helix than an extended structure.

The structures calculated from inexact constraints also ranged in quality depending on the number of constraints. If, for each amino acid, all other amino acids could be classified as in contact (<10 Å away) or not in contact (>10 Å away), the resulting DG-generated structures are on average less than 2 Å RMSD from the crystallographic structure. This result is consistent with those of Havel et al., 1979.

If this proximity information is defined only for interactions between polar residues, the quality of the calculated structures is substantially reduced as the total number of constraints has roughly dropped by a factor of 16. Additional removal of the non-contact information for polar—polar interactions did not dramatically increase the RMSDs for small proteins in the set (i.e. BPTI with 59 residues and alpha bungarotoxin with 74 residues). However, the increase was largest for the two largest proteins: FGF-2 (146 residues) and cyclophilin A (165 residues).

Example 2

FGF Model Studies

The three-dimensional protein structure of FGF-2 was determined using the BS3 crosslinking reagents on FGF-2 followed by RPLC separation and MS analysis (both MALDI and ESI). FGF-2 is a near-optimal system for BS3 intramolecular crosslinking as it is only weakly self-associating in the absence of heparin, highly basic (net charge =+11), and has a primary sequence that is approximately 10% lysines. Venkataraman et al. "Preferential self-association of basic fibroblast growth factor is stabilized by heparin during receptor dimerization and activation." *Proc Natl Acad Sci USA*. 1996 Jan. 23;93(2):845–50. The homobifunctional cross-linker BS3 is a lysine—lysine crosslinker with a six carbon alkyl chain as its spacer arm (length=11.4 Å) and two NHS-ester groups that react with primary amines at physiological pH yielding stable products. The half life of hydrolysis for BS3 is 4–5 hours at pH 7.0. NHS-ester hydrolysis competes for the reaction with primary amines, and therefore the reaction products contain a mixture of a) one end of BS3 covalently linked to the protein, while the other end is hydrolyzed (a dead-end crosslinker), resulting a mass addition of 156.08 Da, and b) two lysines crosslinked with BS3 resulting in a mass addition of 138.08 Da. The description of the reactions as described herein results in a ratio of crosslinked to modified peptides was approximately 1:1.

Chemical Crosslinking

Chemical crosslinking was carried out in very dilute protein solution (5 μM) and the crosslinker to protein ratio was kept at 20:1 to achieve on average one lysine—lysine crosslink per protein. The major reason for this is to avoid any serious perturbation of the protein tertiary structure which would generate crosslinks impossible for the native protein (false distance constraints). It has been shown with crystal structures that one crosslink per protein does not perturb the tertiary and quaternary structure. Haniu et al. "Recombinant human erythropoietin (rHuEPO): cross-linking with disuccinimidyl esters and identification of the interfacing domains in EPO." *Protein Sci*. 1993 Sep.;2(9):1441–51. It is likely that simple single-site modifications would have considerably smaller perturbation on the overall structure than the desired two-site crosslinks. Provided that 50% of the modification comes from crosslinking, the average crosslinks formed per protein is approximately one.

1 mg/ml of FGF-2 protein obtained from an expression system and was dialyzed overnight at 4° C. into a reaction buffer containing 100 mM Hepes pH 7.5, 1 M NaCl and 1 mM EDTA. DTT (10 mM final concentration) was added to the freshly prepared crosslinker and this solution was added to aliquots of the protein-containing reaction buffer. The crosslinkers used were the homobifunctional crosslinkers Bis[sulfosuccinimidyl] suberate (BS3) and Disulfosuccinimidyl-tartarate (sulfo-DST)(Pierce, Rockford, Ill.), with a 20-fold molar excess of crosslinker (100 μM) to FGF-2 protein (5 μM). The reaction was carried out at room temperature from 1–24 hours and quenched with 1M Tris-HCl pH 8.0 to a final concentration of 10 mM. In some cases, the crosslinked FGF-2 was denatured by 8M urea and cysteine residues were protected by adding 50 mM IAM. The modified FGF-2 was concentrated with Centriprep 10 filtration at 4° C. prior to size-exclusion purification and proteolytic digestion.

Size Exclusion Chromatography

Size-exclusion chromatography (SEC) was employed to separate monomeric and dimeric forms of FGF-2 after the crosslinking reaction. The chemical crosslinking reaction can theoretically result in both intramolecular crosslinking (two crosslinked amino acids on one protein) and intermolecular crosslinking (two protein molecules crosslinked to each other). In order to separate monomeric and dimeric forms of crosslinked FGF-2, size exclusion chromatography was performed under denaturing conditions using a Gilson HPLC system equipped with a TosoHaas G2000 (2.0×60 cm). The column was equilibrated with 100 mM citrate buffer (pH 5.0), 8M urea and 1 mM DTT at a flow rate of 1 ml/min. Fractions of monomeric and dimeric protein were collected and concentrated with Centercon 10 filtration at 4° C. Non-denaturing SEC was carried out using two Bio-Silect SEC 125–5 columns (300×7.8 mm). The columns were equilibrated with 100 mM ammonium bicarbonate pH 7.0. The elution was at 1 ml/min and was spectroscopically monitored with a Kratos Spectroflow 783 absorbence detector.

Following SEC separation of dimers from the protein samples, the samples were subjected to SDS-PAGE using 15% gels according to the stacking procedure. Laemmli. "Cleavage of structural proteins during the assembly of the head of bacteriophage T4." *Nature*. 1970 Aug. 15;227(259):680–5. Pre-stained standard protein mixture was purchased from Biorad containing myosin (209 kDa), β-galactosidase (125 kDa), BSA (70 kDa), carbonic anhydrase (42.8 kDa), soybean trypsin inhibitor (32.6 kDa), lysozyme (17.6 kDa) and aprotinin (7.5 kDa) molecular weight proteins.

Capillary HPLC and MALDI-TOF PSD Mass Spectrometry

Figure 16:
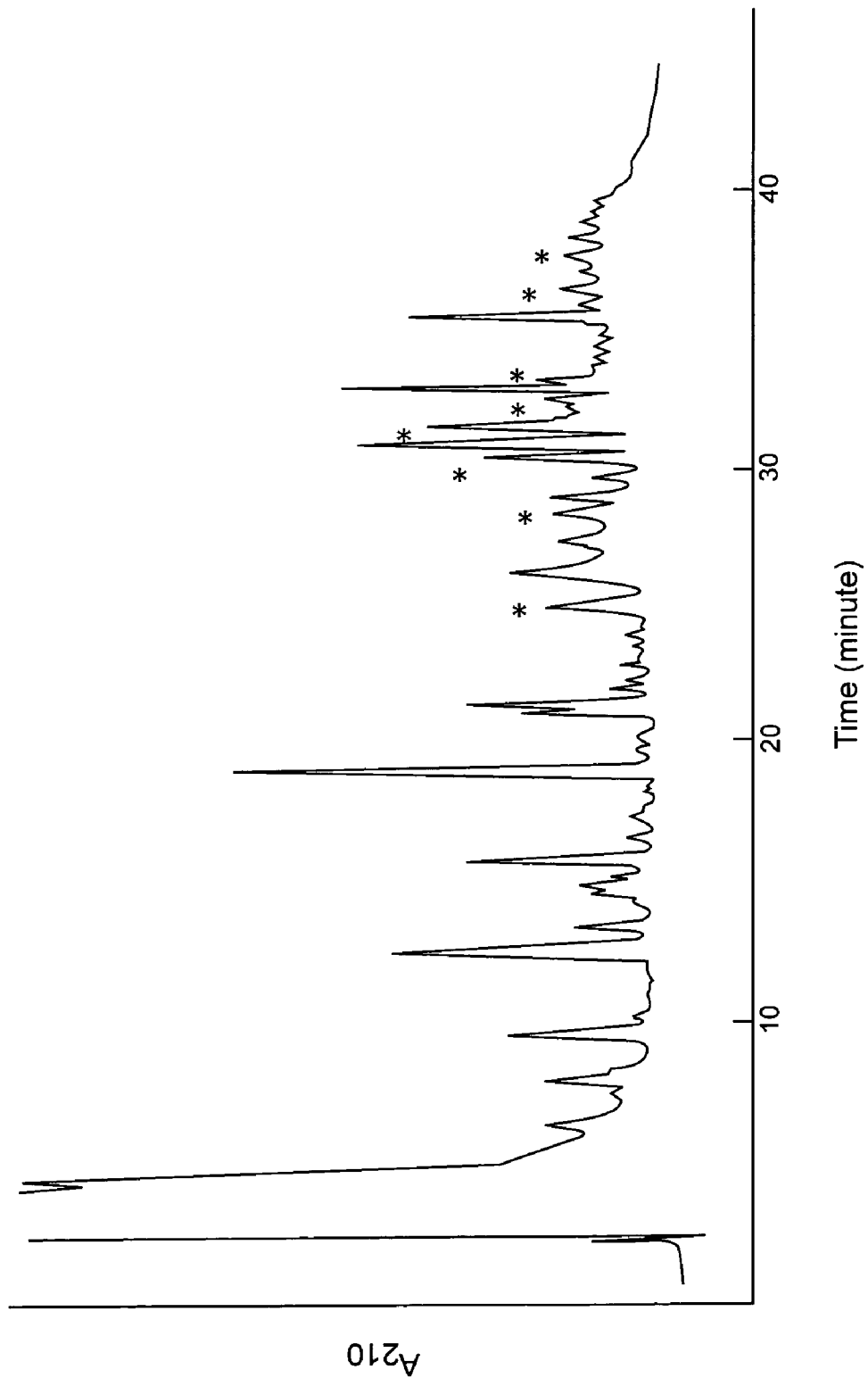
FIG. 16 is an HPLC chromatogram of a tryptic digest of BS3 crosslinked FGF.
Figure 17:
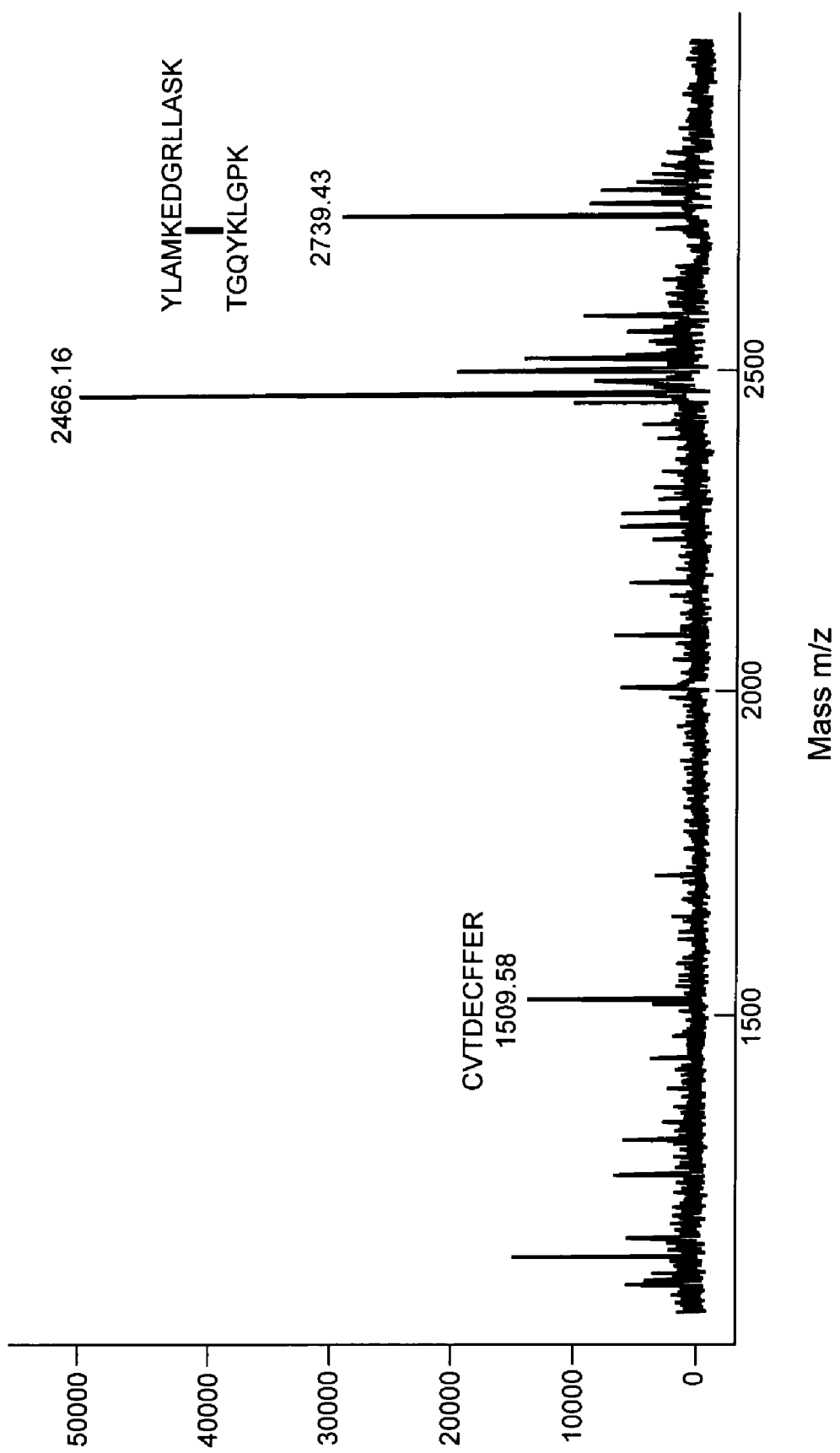
FIG. 17 is a MALDI-TOF spectrum of an HPLC fraction form the tryptic digest of BS3 crosslinked FGF-2.
Figure 18:
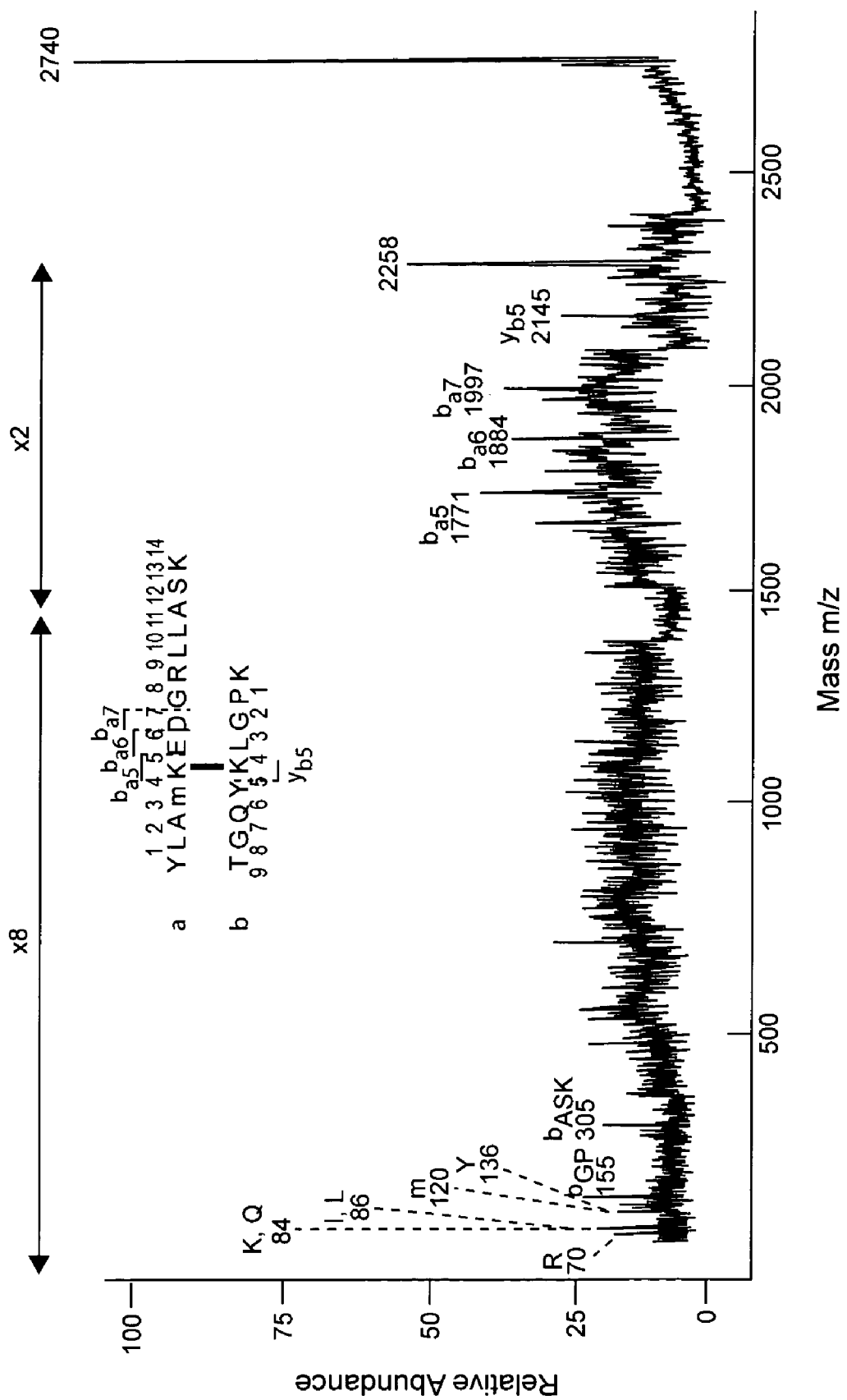
FIG. 18 is a MALDI-TOF PSD spectrum of crosslinked peptide MH+=m/z 2739.4 arising from peptides Tyr73–Lys86 (SEQ ID NO:1) linked to Thr 121–Lys129 (SEQ ID NO:2).

To analyze the crosslinked FGF-2, the monomeric fraction was digested with trypsin. Trypsin digestion was carried out at 37° C. with a trypsin/protein ratio of 1:20. After 16 hours, another aliquot of trypsin (again at a 1:20 ratio of trypsin to protein) was added to the digest and continued to incubate at 37° C. for another 2 hours. The enzymatic digestion was stopped by adding PMSF to a final concentration of 5 mM. The resulting peptide mixture contained unmodified and modified peptides. The chromatogram of the modified FGF-2 tryptic digest FIG. 16 was significantly different than that of the unmodified FGF-2, suggesting the presence of modified peptides. Peak shaded refers to a selected fraction containing several crosslinked peptides including Tyr73-Lys86 linked to Thr 121-Lys129 with an exact mass of m/z=2739.4 whose MALDI and PSD spectrum are shown in FIGS. 17 and 18, respectively. The labeled peaks were identified later by mass spectrometry to be crosslinked peptides. The crosslinked peptides all came out in the later part of the gradient because the BS3 crosslinker arm is hydrophobic.

The identification of the crosslinked peptides involved either on-line LC/MS or off-line reversed phase capillary HPLC, in which case fractions were collected. The mass of the crosslinked FGF-2 mixture was measured on a Voyager DE-STR MALDI-TOF instrument from Perseptive Biosystems, of Foster City, Calif. The instrument used a nitrogen laser (337 nm), delayed extraction optics and an acceleration voltage of 20 kV. In all cases, peptide fractions were mixed with 33 mM α-cyano-4-hydroxycinnamic acid in acetonitrile/methanol (1/1; v/v) and air-dried on a gold-plated MALDI target. Post source decay (PSD) spectra were obtained from the protonated molecular ions (MH+) of selective crosslinked peptide to obtain limited sequence information. For a description of PSD, see Kaufmann et al. "Mass spectrometric sequencing of linear peptides by product-ion analysis in a reflectron time-of-flight mass spectrometer using matrix-assisted laser desorption ionization." *Rapid Commun Mass Spectrom.* 1993 Oct.;7(10):902–10. PSD experiments consisted of selectively gating a precursor peptide ion and analyzing its metastable fragment after focusing through a set of reflectron lens whose voltages were varied in 9–11 steps, with the voltage at each step being reduced to 75% of the previous step. The complete PSD spectrum was produced by stitching the individual focused segments together. Mass calibration in PSD mode was performed using the fragment ions from a standard peptide, ACTH 18–39. A broad peak was observed with an average mass shift (compared to the unmodified FGF-2) of around 250 Da.

The assignments of an intra—(K46-K52) and an interpeptide (K26-K46) crosslinks are typical examples of how each of the 18 crosslinks was assigned. FIG. 17 shows a MALDI-TOF spectrum of one of the fractions from the tryptic digest. Each spectrum was calibrated with a close approximate external standard. A mass list was generated for each spectrum and the mass assignments were done using the in-house software ASAP, as described above in the computational features of the invention. Briefly, this program can identify crosslinked protein fragments based on the predicted fragmentation of a protein with a specific enzyme.

Figure 19A:
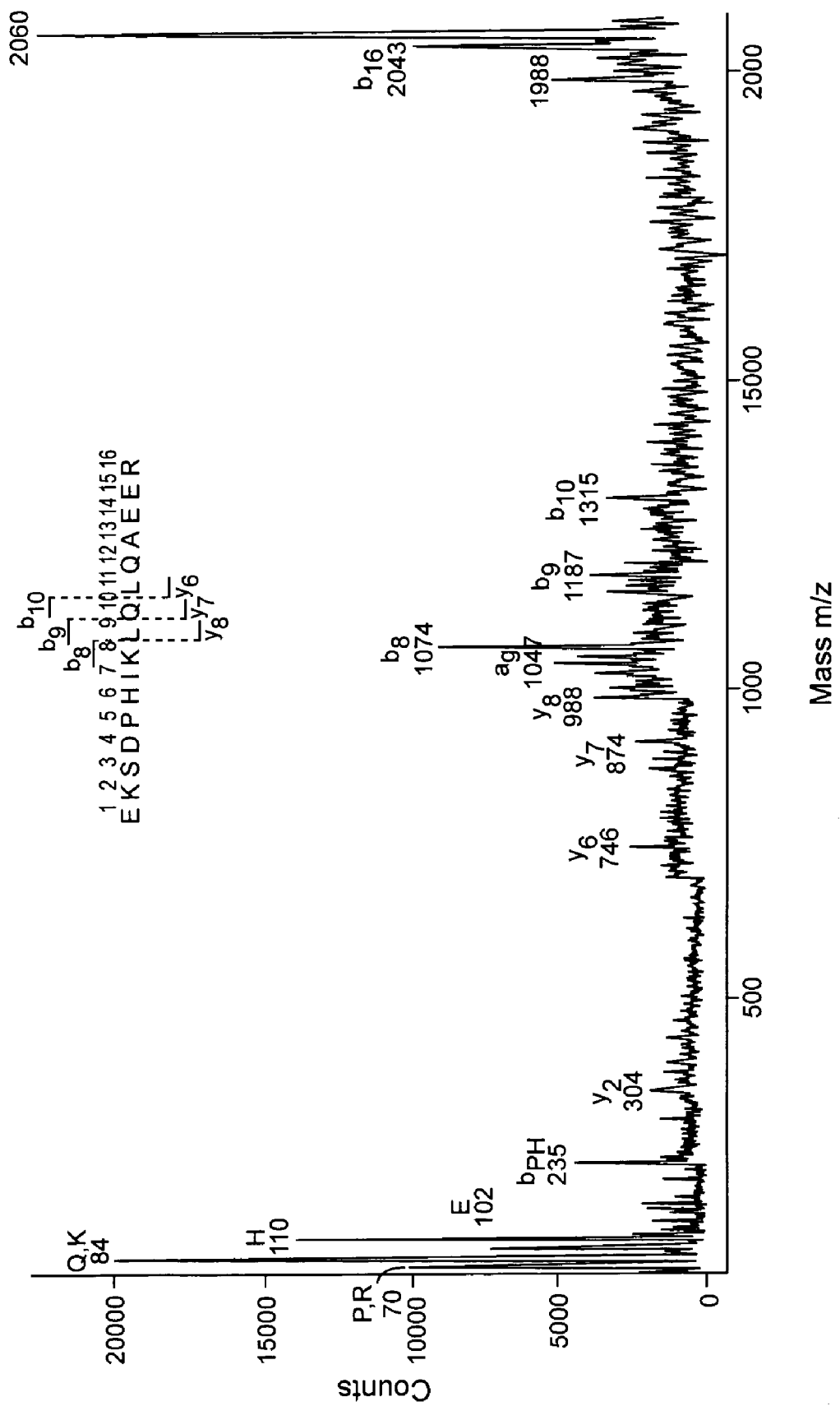
FIGS. 19A and 19B are MALDI-TOF spectra of intramolecular crosslinked peptide (SEQ ID NO:3) at MH+=m/z 2059 (A) and intermolecular crosslinked peptide (SEQ ID NO:4) and (SEQ ID NO:5) at MH+=m/z 2565 (B).

Three tryptic peptides were assigned, one intrapeptide crosslink and one interpeptide crosslink within 100 ppm mass error in this particular fraction. The three tryptic peptides are easy to identify. The masses match peptides 27N-33R (M+H+=810.49), 111Y–119K (M+H+=1116.633) and 110K-119K (M+H+=1224.73). Ion m/z 2059.05 was identified as an intra-peptide crosslink. The total mass of this ion is the sum of the mass of the peptide 45E-60R (M+H+=1921.00 Da) and the mass of the crosslinker arm (138.08 Da). Since there are only two internal lysines in this peptide (EKSDPHIKLQLQAEER), lysine 46 is presumably crosslinked to lysine 52. This assignment is confirmed by a MALDI-PSD (Post Source Decay) experiment (FIG. 19a). In the low molecular weight region, amino acid ammonium ions of P/R, Q/K, H, E, I/L were observed, which gave the amino acid composition of the peptide. Three N-terminal fragments (m/z 1074, m/z 1187, m/z 1315) and three C-terminal fragments (m/z 988, m/z 874, m/z 746) that were consistent with the assignment of the peptide and the crosslinking position. The PSD data thus confirmed our assignment of ion m/z 2059.05 as peptide 45E-60R with lysine 46 crosslinked to lysine 52.

Figure 19B:
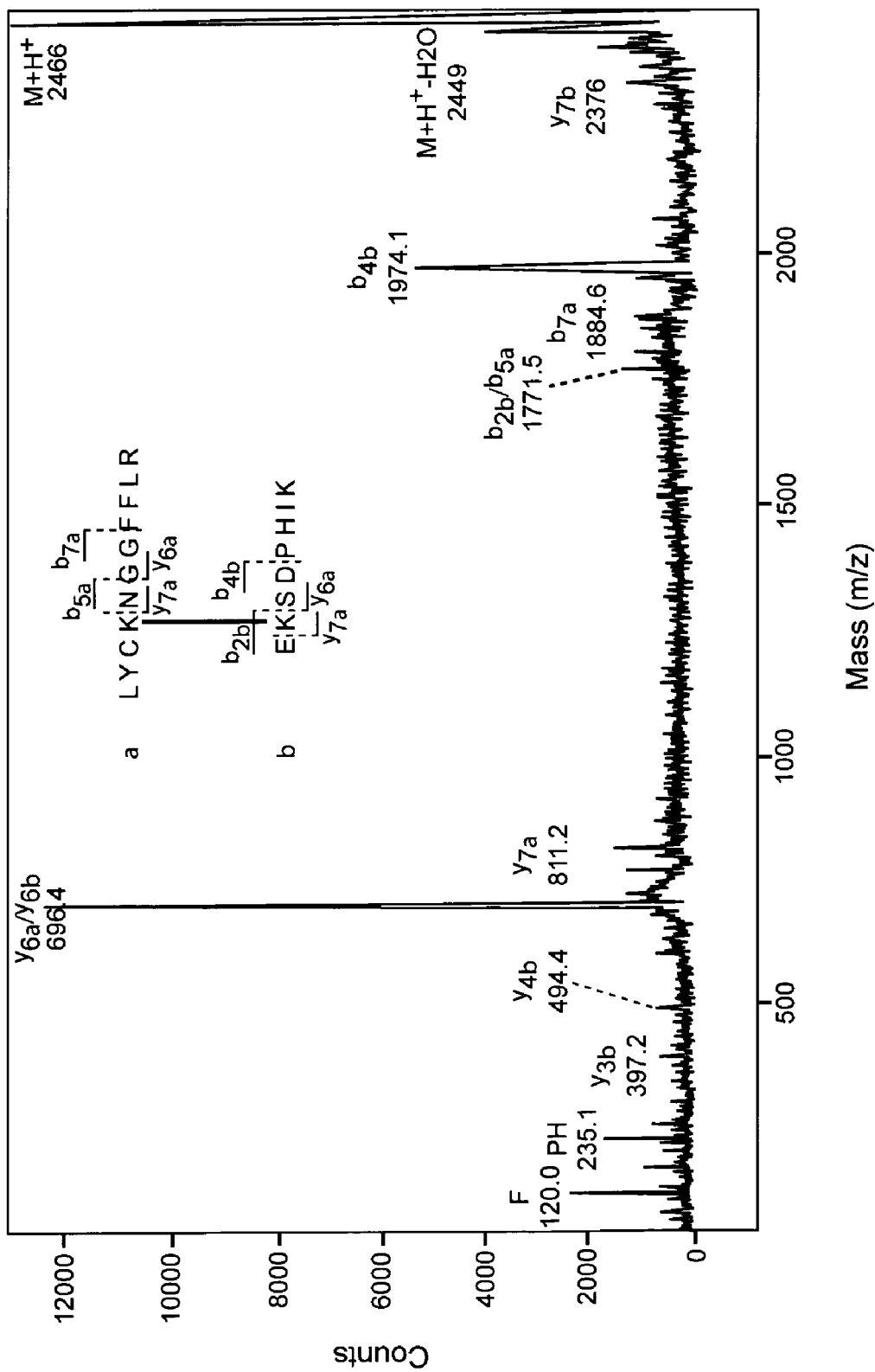

Ion m/z 2465.31 was assigned as an inter-peptide crosslink. The total mass is the sum of two tryptic peptides 23L-33R (M=1316.66 Da), 45E-52K (M=952.487 Da), crosslinker arm (M=138.083 Da), and one proton. From surface-labeling experiments (data not shown), the lysine which is modified by the NHS ester was not recognized by trypsin and was not cleaved, which shows that the C-terminal lysine 52 cannot be the site of modification. The only possibility, therefore, is a crosslink between lysine 26 and lysine 46. PSD of the selected parent ion m/z 2465.31(FIG. 19b) showed the ammonium ions for P/R, K, H, R, F, and Y in the low molecular weight region. "α" is used to represent peptide chain 23L-33R and "β" to represent peptide 45E-52K. The most abundant fragment ion was m/z 696.4 matching both y6$_\alpha$, and y6$_\beta$. The ion m/z 1974.7 matched fragment b4$_\beta$. Ninety percent of the fragments in the PSD spectrum were consistent with the assignment, thus confirming that peptides 23–33 and 45–52 were crosslinked at K26–K46.

TABLE 1

BS3 Crosslinked tryptic peptides from FGF-2.

| K-K Crosslink | Crosslinked Peptide(s) | Measured M + H + (D) | Theoretical M + H + (D) | Error (ppm) |
|---|---|---|---|---|
| 21–26 | 19–33 | 1952.114 | 1952.014 | 51.2 |
| 21–125 | 19–26, 121–129 | 2151.268 | 2151.172 | 44.6 |
| 21–135 | 19–22, 130–145 | 2327.300 | 2327.293 | 3.1 |
| 26–46 | 23–33, 45–52 | 2465.252 | 2465.257 | 2.1 |
| 46–52 | 45–60 | 2059.050 | 2059.075 | 12.1 |
| 46–119 | 40–52, 111–120 | 2889.637 | 2889.445 | 66.4 |
| 46–125 | 40–52, 120–129 | 2764.484 | 2764.519 | 12.7 |
| 46–145 | 45–52, 136–146 | 2268.396 | 2268.240 | 68.8 |
| 77–86 | 67–97 | 3839.788 | 3839.762 | 4.7 |
| 77–110 | 73–81, 110–119 | 2464.480 | 2464.267 | 86.4 |
| 77–119 | 73–81, 111–120 | 2408.159 | 2508.273 | 45.5 |
| 77–125 | 73–81, 121–129 | 2226.923 | 2227.151 | 98.9 |
| 77–135 | 73–81, 130–145 | 2894.410 | 2894.530 | 41.4 |
| 110–119 | 110–125 | 2115.960 | 2116.115 | 73.3 |
| 110–135 | 110–119, 130–145 | 3056.610 | 3056.662 | 17.0 |
| 119–125 | 111–120, 121–129 | 2401.256 | 2401.300 | 18.2 |
| 119–129 | 111–120, 126–135 | 2392.370 | 2392.311 | 24.8 |
| 125–129 | 121–135 | 1697.960 | 1697.915 | 26.5 |

On-Line HPLC/ESI-TOF MS.

Some tryptic digests were also analyzed using on-line HPLC and electrospray ionization time-of-flight (ESI-TOF) mass spectrometry. The peptides were separated by RP-HPLC and eluted directly into the source of mass spectrometer. The ESI-TOF mass spectra were acquired using Mariner electrospray ionization time-of-flight mass spectrometer coupled to an Applied Biosystems 140B solvent delivering system with a Applied Biosystems 759A absorbence detector. Solvent A contained 0.1% formic acid in H$_2$O. Solvent B contained 0.05% formic acid in 5/2 of Ethanol/Propanol. The gradient varied from 10%–60% B in 70 minutes.

In general, a mass accuracy of 100 ppm was achieved with either MALDI-TOF or ESI-TOF mass spectrometry. Higher mass accuracy up to 20 ppm was achieved using internal calibration. In all, 18 masses were assigned uniquely to crosslinked peptides.

Constrained Threading

A "constrained threading" approach was used for fold recognition. The first step was to submit the bovine FGF-2 sequence (FGF2_BOVIN) to the threading program 123D for fold prediction. Alexandrov et al., 1996. The 123D program returned the top scoring 20 sequence-structure alignments found upon threading a database of 635 sequence-unique proteins. Hobohm et al., 1997. The 20 best-scoring sequence-structure pairs found by the 123D threading algorithm for the FGF-2 sequence are listed in Table 2:

TABLE 2

| Rank | Name | Fold Family | % Identity | Function |
|---|---|---|---|---|
| 1 | FGF-2 | β-trefoil | 98.63 | Cytokine |
| 2 | D-UTPase | β-clip | 7.83 | UTP hydrolysis |
| 3 | PLC-gamma-1 | SH2-like | 8.22 | Phosphoric diester hydrolase |
| 4 | Endoglucanase C | Galactose-binding | 11.59 | Cellulose degradation |
| 5 | Interleukin 1-β | β-trefoil | 12–73 | Cytokine |
| 6 | NTP pyrophospho hydrolase | NTP purophospho-rylase | 9–27 | DNA repair |
| 7 | TBP | TBP-like | 10–27 | Transcriptional regulation |
| 8 | Gastrotropin | Lipocalin | 7.05 | Fatty acid-binding |
| 9 | Guanylate kinase | P-loop | 12.44 | GMP phosphorylation |
| 10 | PYP | Profilin-like | 8.84 | Photoreceptor |
| 11 | Cytochrome C4 | Cytochrome C | 12.57 | Electron transfer |
| 12 | Hisactophilin | β-trefoil | 8.55 | Actin-binding |
| 13 | Aspartate carbomoyltransferase | Ferredoxin-like | 9.76 | Carbamoyl transferase |
| 14 | Glutathione peroxidase | Thioredoxin-like | 11.11 | Oxidoreductase |
| 15 | DSBA | Thioredoxin-like | 8.42 | Disulfide bond formation |
| 16 | Phospholipase A2 | Phospholipase A2 | 9.46 | Carboxylic ester lipase |
| 17 | Paired protein | 3-helix bundle | 12.67 | Transcriptional regulation |
| 18 | Retinol binding protein | Lipocalin | 9.09 | Retinol transport |
| 19 | ASV integrase | Ribonuclease H-like | 7.74 | DNA integration |
| 20 | Nucleotide diphosphate kinase | Ferredoxin-like | 8.81 | Phosphotransferase |

Each pair defines a structural model for the FGF-2 sequence. Three β-trefoil proteins are in the top 20 sequence-structure pairs, ranked at positions 1 (FGF-2: 4FGF), 5 (IL-1β), and 12 (hisactophilin: 1HCE). The FGF-2 structure 4FGF shares greater than 98% identity with the recombinant sequence, which in part explains why it was ranked # 1 by the threading algorithm. However, if the structure of a fibroblast growth factor was not in the threading database, the threading algorithm would mis-predict the fold family of FGF-2 to be that of D-UTPase, a β-clip protein.

Correction for Distance Restraints

These 20 threading models were then evaluated for their fit to our experimentally-derived distance constraints by calculating Et, the total constraint error, using the equation:

$$E_t = \sum_{j=0}^{j<=i} 0 \text{ if } d_j <= d_o, d_j - d_o \text{ if } d_j > 0$$

$E_t$ is the total constraint error, i is the number of distance constraints, $d_o$ is the pairwise distance separation, and $d_j$ is the pairwise distance defined by the structure for the two residues in constraint j. Thus $d_j$ is the distance observed in the candidate threading model. If $d_j$ is less than or equal to the distance $d_j$ defined by the length of the linker arm, then there is no constraint error contributed by that constraint j. If $d_j$ is greater than $d_j$, then the constraint error is defined by the difference between these distances. A distance of 23.85 Å is the theoretical maximum through-space distance which can be spanned by two lysines crosslinked by BS3. Constraints in some cases could not be defined due to unresolved regions in the crystallographic structure or a gap in the sequence alignment. Only sequence-structure models which had >50% of the pairwise constraints were evaluated to avoid considering models with artificially low constraint errors. The top 20 threading models were ranked in order of increasing constraint error (Table 3).

TABLE 3

Top 20 Models Re-Ranked by Constraint Error

| Name | Fold Family | % ID | 123D Rank | Error | Function |
|---|---|---|---|---|---|
| FGF-2 | β-trefoil | 98.6 | 1 | 0.00 | Cytokine |
| Interleukin 1-β | β-trefoil | 12.7 | 5 | 0.00 | Cytokine |
| Gastrotropin | Lipocalin | 7.1 | 8 | 3.03 | Fatty-acid binding |
| Hisactophilin | β-trefoil | 8.6 | 12 | 5.81 | Actin-binding |
| Guanylate kinase | P-loop | 12.4 | 9 | 8.04 | GMP phosphorylation |
| NTP pyrophosphohydrolase | NTP pyrophosphohydrolase | 9.3 | 6 | 14.93 | DNA repair |
| Glutathione peroxidase | Thioredoxin | 11.1 | 14 | 17.39 | Glutathione oxidation |
| Retinol binding protein | Lipocalin | 9.1 | 18 | 17.57 | Retinol-binding |

TABLE 3-continued

Top 20 Models Re-Ranked by Constraint Error

| Name | Fold Family | % ID | 123D Rank | Error | Function |
| --- | --- | --- | --- | --- | --- |
| Nucleoside diphosphate kinase | Ferridoxin-like | 8.8 | 20 | 18.85 | NDP phosphorylation |
| Cytochrome C4 | Cytochrome C | 12.6 | 11 | 22.19 | Electron transfer |
| Aspartate carbomoyl transferase | Ferridoxin-like | 9.8 | 13 | 23.20 | Carbamoyl transferase |
| D-UTPase | β-clip | 7.8 | 2 | 28.54 | UTP hydrolysis |
| DSBA | Thioredoxin | 8.4 | 15 | 29.20 | Disulfide bond formation |
| ASV integrase | Ribonuclease H-like | 7.8 | 19 | 29/38 | DNA integration |
| Endoglucanase C | Galactose binding | 11.6 | 4 | 34.66 | Cellulose degradation |
| TBP | TBP-like | 10.3 | 7 | 41.20 | Transcription |
| PLA2 | PLA2 | 9.5 | 16 | 56.36 | Carboxylic ester lipase |
| Paired protein | 3-helix bundle | 12.7 | 17 | 144.56 | |

Two structural models with <50% of the constraints defined due to gaps in the alignment or unresolved regions in the crystal structure templates were discarded (2PHY, 2PLDA). After calculation of the constraint errors, members of the β-trefoil fold family which were ranked 1, 5, and 12 by the threading algorithm were re-ranked as 1,2, and 4 in Table 3. They are respectively FGF-2, IL-1β, and hisactophilin. In this case, if the structure of FGF-2 was unknown, FGF-2 would be correctly predicted to share the same fold as IL-1β even though the sequence identity of the alignment of FGF-2 and IL-1 is less than 13 percent.

The structure ranked #3, fatty acid binding protein (1EAL), is a member of the lipocalin fold family, which shares many characteristics with the α-trefoil family. The lipocalin family is characterized by a closed or open beta barrel with a meander motif. Murzin et al. 1995. The β-trefoil fold family similarly contains a closed beta barrel with a meander motif and a hairpin triplet. The structure of fatty acid binding protein is an open 10-stranded beta barrel with a beta-hairpin insertion and is alignable to FGF-2 with an RMSD of 3.6 Å over 47 residues. Holm et al. "Protein Structure Comparison by Alignment of Distance Matrices." *J Mol Bio.* 1993 233:123–38. The other member of the lipocalin fold family, retinol binding protein (1HBQ), is ranked at position 8 and contains an 8-stranded closed beta barrel.

Reranking the top scoring sequence-structure pairs based on constraint error makes a strong prediction for the β-trefoil fold family. Members of this family occupy 3 of the top 4 positions in the list. Additionally it is the only family with a structural representative (IL-1β) completely consistent with experimental data. Assuming the FGF-2 structure was unknown, the IL-1β structure would be a reasonable starting point to construct a homology model for the FGF-2 sequence.

Spectral Assignment

A mass spectrum analysis program was developed to assist in the interpretation of our experimental data. The program requires input in the form of: a SwissProt sequence, a mass/charge list, the crosslinker mass, the maximum allowed mass error, a proteolytic enzyme, a mass type, a maximum charge state, and a minimum peak abundance. A virtual proteolytic library of peptides is constructed based on the known protein sequence and proteolytic specificity. Each peptide in the library is indexed by either its monoisotopic or average mass. Amino acid modifications, intrapeptide labeling, and/or intrapeptide crosslinking are represented in the virtual library. For each unassigned mass, the program searches the virtual library for representatives with masses within the user-defined error threshold. If no matches are found, the program combinatorially searches the library for crosslinkable peptide pairs with an additive mass within the error threshold of the experimental mass. For each mass, ASAP lists the possible assignment(s) and the mass error for each assignment relative to the theoretical mass.

Homology Modeling

The distance constraint information derived from the lysine—lysine crosslinks was selective for structures similar to that of FGF-2 present in a set of top-scoring threading models. Specifically, the structure of IL-1β was the most compatible with the experimentally-derived distance constraints (ranked second to FGF-2) and shares the same fold as FGF-2 (β-trefoil). The threading alignment of FGF-2 to the IL-1β structure was then used as a starting point in the construction of a 4.8 Å homology model of FGF-2.

Figure 21:
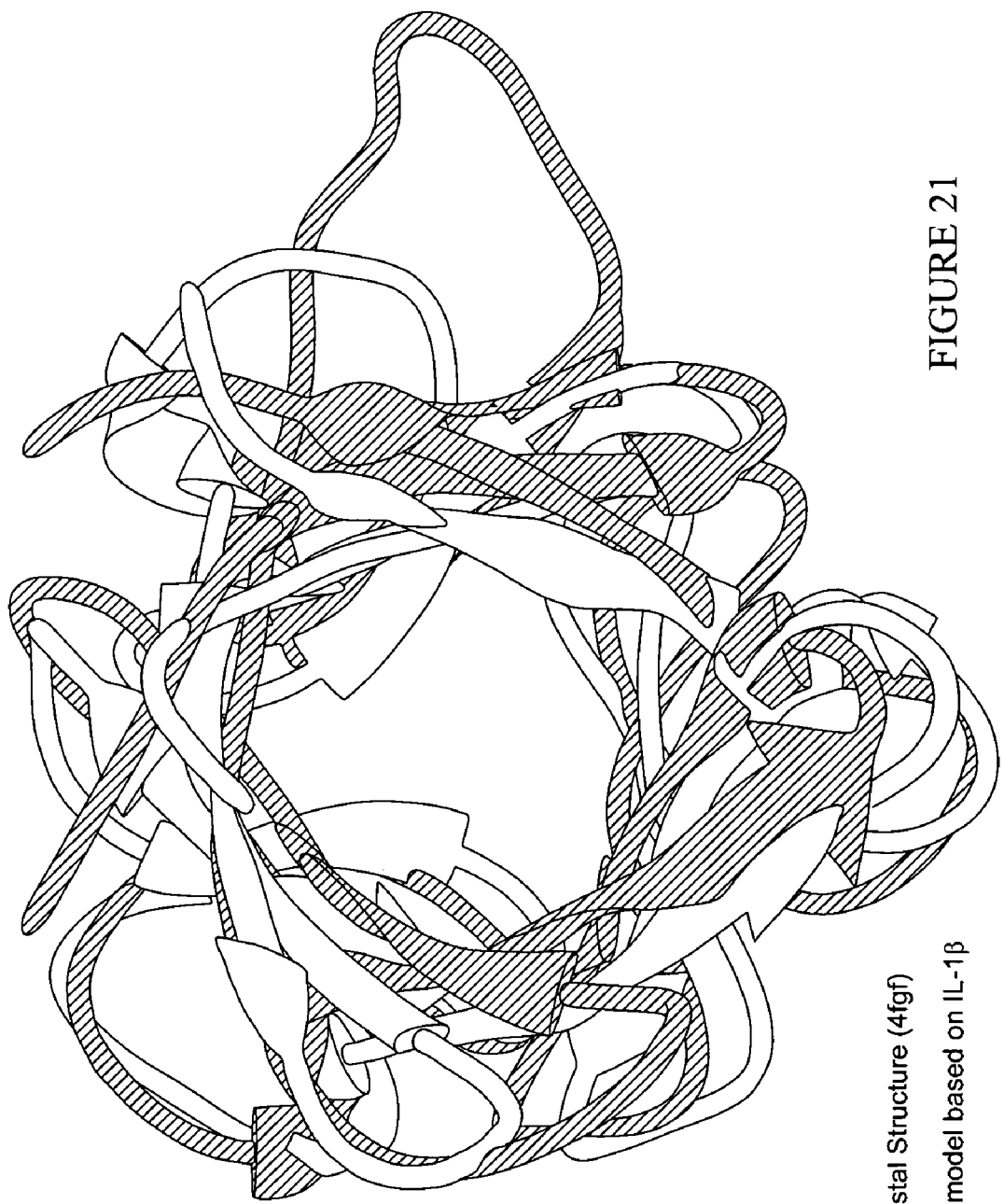
FIG. 21 illustrates the structural alignment of the FGF-2 homology model to FGF-2 (4FGF).

The model was based on the threading alignment of FGF-2 sequence to the IL-1β structure. FIG. 20 shows a threading alignment of IL-1β and FGF-2 used for homology modeling. The threading alignment defined 119 amino acids in the homology model. The total backbone RMSD of a model built based on this alignment is 8.36 Å. If the poorly-aligned N-terminal region is removed from the alignment, the RMSD improves to 4.76 Å over 98 amino acids. FIG. 21 illustrates the match between structure after homology modeling and the actual protein structure. This RMSD is equivalent to that expected for, on average, a 1 amino acid frameshift in the sequence alignment.

The model captures the salient features of the FGF-2 structure even though FGF-2 and IL-1β share less than 20% sequence identity. The beta strands at the core of the FGF-2 structure are positioned correctly. Not surprisingly, the sequence alignment and modeling errors occur mainly in the loop regions, regions that are generally difficult to model accurately for sequences sharing limited homology. Hilbert et al. "Structural relationships of homologous proteins as a fundamental principle in homology modeling." *Proteins.* 1993 17(2):138–51. The N-terminal 20 amino acids are also poorly aligned by the threading algorithm. The "correct" alignment, as defined by a DALI structural alignment of the IL-1 and 4FGF structures (2.7 Å RMSD over 101 residues), is substantially different in the N-terminal region. *Holm et al.,* 1993. Gaps left in the structure due to insertions of IL-1β relative to FGF-2 were closed with 100 steps of energy minimization using Tripos Sybyl 6.4. The root-mean-square deviation (RMSD) of the model to the crystal structure backbone was calculated by aligning equivalent residues in the model to those in the crystal structure. The lowest RMSD we could expect for our homology model corresponds to this structural alignment.

In most cases, we subsequently confirmed the peptide crosslink assignment by performing PSD analysis of individual peptides, which often provided information as to the precise linkage positions. These data were then used to tabulate a set of distance constraints among these lysine residues.

This experimental data has shown that it is possible, in single experiments, to resolve to the residue level 18 lysine—lysine crosslinks in FGF-2, a small globular protein. The lysine-to lysine proximity data, when transformed into very conservative residue-to-residue distances, are sufficient to identify correctly the fold family of FGF-2. While additional crosslinks would be needed to determine a de novo low resolution, three dimensional structure of this protein, the lysine crosslinking results and the known structure of a FGF-2 homolog can be used to produce a 4.8 Å structure of FGF-2. This technology can be used on multiple proteins of varying size and complexity, and uses ≦1 mg of protein.

Example 3

HIV-1 Integrase

HIV-1 integrase is a 288 amino acid protein containing 3 structural domains: a zinc-finger N-terminal domain, the catalytic core, and a non-specific DNA binding C-terminal domain. Although the—and C-terminal domains have been solved individually by NMR, and the core domain has been solved by X-ray crystallography (Dyda et al, 1994; Lodi et al., 1995; Cai et al., 1997; Goldgur et al., 1998), the full-length structure of HIV integrase has not been determined.

Intramolecular crosslinking with BS3 was applied to the full-length HIV-I integrase protein. The protocol was the same as that used for FGF-2, e.g., crosslinking followed by size exclusion chromatography, proteolysis, and LC-MS. The purpose of this experiment was not to determine the fold family of integrase, but rather to map the domain—domain interactions within the full-length structure. Theoretically, less than 9 inter-domain crosslinks are required (~3 per domain pair) to determine the arrangement of the three domains within the integrase monomer.

One crosslinking reaction generated 5 inter-domain crosslinks. The crosslinked lysines were K34–K264, K42–K159, K42–K186, K42–K236, and K186–K236. Two crosslinks were N-terminal domain/core domain crosslinks, two were N-terminal domain/C-terminal domain crosslinks, and one was a core domain/C-terminal domain crosslink. Each crosslink defined the upper limit on the distance between the two lysines involved in the linkage. Using the distance information derived from the 5 crosslinks, the structures of the 3 domains, and constraints bridging the gaps between domains, we were able to calculate a unique arrangement for the three integrase domains using distance geometry.

Example 4

CMP-NeuAc Synthetase

A set of crosslinking experiments was also employed to determine the conformation of CMP-NeuAc synthetase (CNase), a *Haemophilus* protein with unknown tertiary structure. The protein has previously isolated and expressed and the enzymatic mechanism determined. Tullius et. al. "Covalent modification of Lys 19 in the CTP binding site of cytidine 5'-monophosphate N-acetylneuraminic acid synthetase." *Protein Sci.* 1999 Mar.;8(3):666–75; Samules, et al. "Investigation of the Kinetic Mechanism of Cytidine 5'-Monophosphate N-Acetylneuraminic Acid Synthetase from *Haemophilus ducreyi* With New Insights On Rate-limiting Steps from Product Inhibition Analysis." *Biochemistry.* 1999 38(19) 6195–203. CNase catalyzes the reaction of CTP and sialic acid (or NeuAc) to form the nucleotide-sugar donor substrate, CMP-NeuAc, which in turn adds sialic acid onto terminal galactose residues in the lipooligosaccharides of infectious bacteria. The addition of sialic acid is an important virulence mechanism in bacteria, and the CNase enzymes are potentially attractive targets for drug development.

The CNase molecule was also examined using BS3 as a crosslinker. The crosslinked protein and further analysis identified six crosslinked peptides in a single BS3 experiment. (Table 4) Using these limited Lys—Lys distance constraints in conjunction with threading methods, we were not able to identify a unique fold family in the database, although β-barrel proteins scored consistently high. Additional distance constraints using other homo- and heterobifuctional reagents are then used to identify not only the fold-family of CNase, but also a full tertiary structure in the 3–5 Å error range.

TABLE 4

BS3-linked peptide crosslinks in CNase

| Lys-Lys Crosslink | Start - End | Measured M + H⁺ | Error (ppm) |
|---|---|---|---|
| 17–19 | 15–32 | 2005.171 | 5.2 |
| 14–17 | 11–19 | 1041.588 | 6.7 |
| 164–167 | 163–170 | 1157.686 | 14.9 |
| 14–167 | 165–170, 4–17 | 2295.251 | 61.3 |
| 17–167 | 15–19, 165–170 | 1460.853 | 3.4 |
| 17–164 | 15–19, 163–167 | 1310.824 | 14.6 |

Figure 22A:
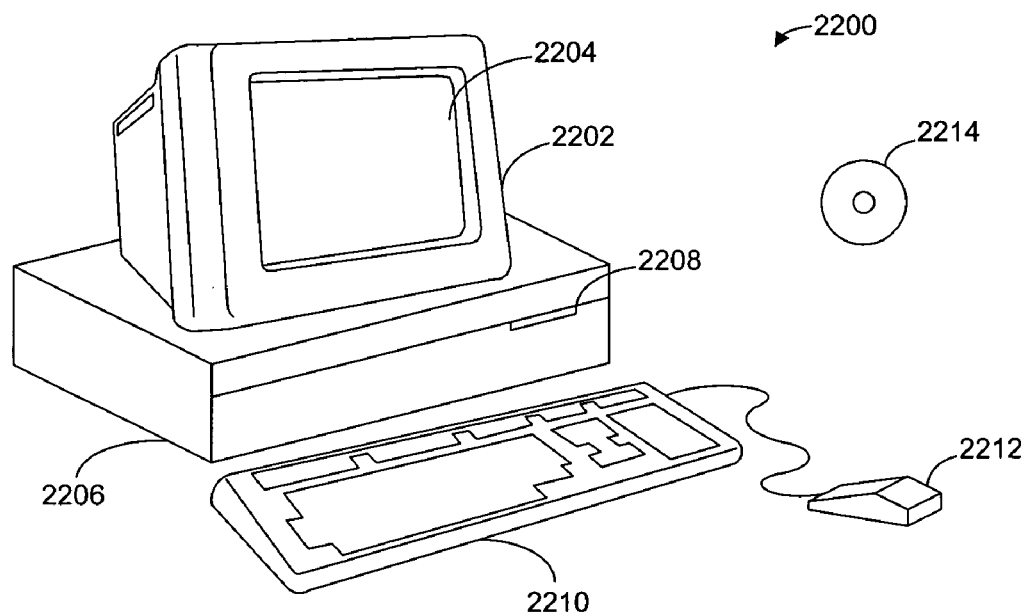
FIGS. 22A and 22B illustrate a computer system suitable for implementing embodiments of the present invention.
Figure 22B:
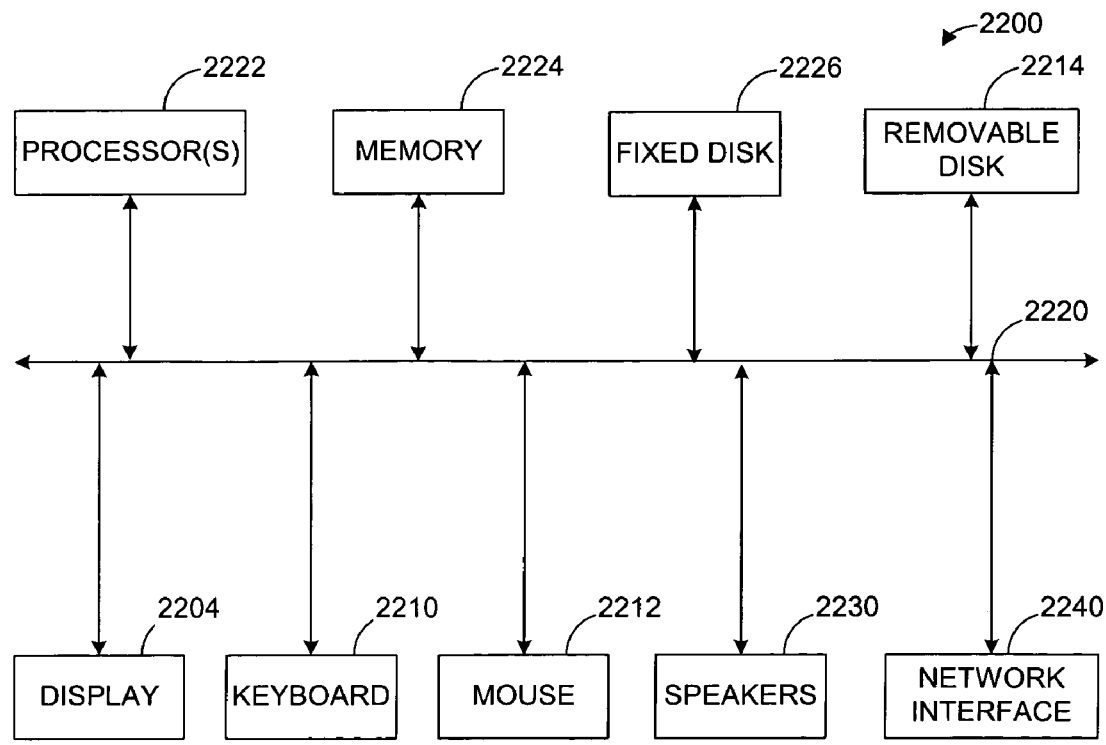

FIGS. 22A and 22B illustrate a computer system 2200 suitable for implementing embodiments of the present invention. FIG. 22A shows one possible physical form of the computer system. Of course, the computer system may have many physical forms ranging from an integrated circuit, a printed circuit board and a small handheld device up to a huge super computer. Computer system 2200 includes a monitor 2202, a display 2204, a housing 2206, a disk drive 2208, a keyboard 2210 and a mouse 2212. Disk 2214 is a computer-readable medium used to transfer data to and from computer system 2200.

FIG. 22B is an example of a block diagram for computer system 2200. Attached to system bus 2220 are a wide variety of subsystems. Processor(s) 2222 (also referred to as central processing units, or CPUs) are coupled to storage devices including memory 2224. Memory 2224 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A fixed disk 2226 is also coupled bi-directionally to CPU 2222; it provides additional data storage capacity and may also include any of the computer-readable media described below. Fixed disk 2226 may be used to store programs, data and the like and is typically a secondary storage medium (such as a hard disk) that is slower than primary storage. It will be appreciated that the information retained within fixed disk 2226, may, in appropriate cases, be incorporated in standard fashion as virtual memory in memory 2224. Removable disk 2214 may take the form of any of the computer-readable media described below.

CPU 2222 is also coupled to a variety of input/output devices such as display 2204, keyboard 2210, mouse 2212 and speakers 2230. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. CPU 2222 optionally may be coupled to another computer or telecommunications network using network interface 2240. With such a network interface, it is contemplated that the CPU might receive information from the network, or might output information to the network in the course of performing the above-described method steps. Furthermore, method embodiments of the present invention may execute solely upon CPU 2222 or may execute over a network such as the Internet in conjunction with a remote CPU that shares a portion of the processing.

In addition, embodiments of the present invention further relate to computer storage products with a computer-readable medium that have computer code thereon for performing various computer-implemented operations such as inputting assay data, rendering that data in color graded representations in a graphical user interface, and acting on user inputs to affect display parameters of the data. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs), ROM and RAM devices, and signal transmission media for delivering computer-readable instructions, such as local area networks, wide area networks, and the Internet. Examples of computer code include machine code, such as produced by a compiler, and files containing higher level code that are executed by a computer using an interpreter. The invention also pertains to carrier waves and transport media on which the data and instructions of this invention may be transmitted.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Although various details have been omitted for brevity's sake, obvious design alternatives may be implemented. Therefore, the present examples are to be considered as illustrative and not restrictive, and the invention is not to be limited to the details given herein, but may be modified within the scope of the appended claims.

What is claimed is:

1. A method of determining the tertiary structure of a protein, comprising the steps of:

imposing physical distance constraints between residues of the protein by cross-linking the protein;

fragmenting the cross-linked protein into molecular fragments;

subjecting the fragments to an identification procedure comprising a mass spectrometric analysis to identify sequences of the fragments;

analyzing identification information obtained from the identification procedure to identify cross-link fragments in the protein;

providing a set of candidate three-dimensional conformations for the protein's primary sequence; and applying physical distance constraint information associated with the cross-linking for the identified crosslink fragments to the candidate three-dimensional conformations to rank said three-dimensional conformations and selecting one or more of said three-dimensional confirmations based on the ranking, wherein the tertiary structure of the protein is thereby determined.

2. The method of claim 1, further comprising:

conducting homology modeling analysis of the selected one or more three-dimensional conformations that best fit the distance constraint information associated with the cross-linking.

3. The method of claim 1, wherein the reaction with the crosslinker is optimized to produce an avenge number of one crosslinker modification per macromolecule.

4. A method of determining the tertiary structure of a protein, comprising the steps of:

reacting a protein to be analyzed with at least one crosslinking reagent, said reagent comprising at least two reactive groups;

enriching the reaction product for molecules having intramolecular crosslinks;

carrying out proteolysis on the enriched reaction product to yield protein fragments;

subjecting the protein fragments to peptide identification analysis comprising a mass spectrometric analysis to identify sequences of the protein fragments;

analyzing information obtained from the peptide identification analysis to identify cross-link fragments in the protein;

providing a set of candidate three-dimensional conformations for the protein's primary sequence; and applying physical distance constraint information associated with the cross-linking reagent for the identified cross-link fragments to the candidate three-dimensional conformations to rank said three-dimensional conformations and selecting one or more of said three-dimensional conformations based on the rankings, wherein the tertiary structure of the protein is thereby determined.

5. The method of claim 4, wherein the crosslinking reagent is a bifunctional crosslinker.

6. The method of claim 5, wherein the crosslinking reagent is an amine-specific homobifunctional crosslinker.

7. The method of claim 4, wherein the protein is reacted with a plurality of crosslinking agents having different specificities for reactive sites on the protein.

8. The method of claim 4, wherein the protein is reacted with a plurality of crosslinking reagents having varying lengths between reactive groups.

9. The method of claim 4, wherein the reaction product is enriched for molecules having intramolecular crosslinks by physical removal of proteins having intermolecular crosslinks.

10. The method of claim 4, further comprising:

conducting homology modeling analysis of the selected one or more the three-dimensional conformations that best fit the distance constraint information associated with the cross-linking reagent.

11. The method of claim 1 or 4, wherein analyzing information obtained from the peptide identification analysis comprises constructing a virtual library of proteolyzed product which library is indexed by a criteria selected from the group consisting of monoisotopic data and average mass data.

12. The method of claim 1 or 4, wherein providing a set of candidate three-dimensional conformations for the full primary sequence of the protein employs a threading program.

13. The method of claim 1 or 4, wherein applying physical distance constraint information associated with the cross-linking reagent for the identified cross-link fragments is performed with the use of an equation $$E_t = \sum_{j=0}^{j<=i} 0 \text{ if } d_j <= d_o, d_j - d_o \text{ if } d_j > 0$$

wherein $E_t$ is the total constraint error, $d_o$ is the pairwise distance separation, $d_i$ is the pairwise distance defined by the structure by constraint j and i is the total number of distance constraints.

14. The method of claim 1 or 4, further comprising performing an initial selection of the candidate three-dimensional conformations by assessing said conformations' compatibility with computed physical properties for the conformations.

15. The method of claim 14, wherein assessing said conformations' compatibility with computed physical properties for the conformations comprises using at least one technique selected from among: calculating the distribution of hydrophobic/hydrophilic amino acids; mapping a hydrogen-bond network; locating disulfide bridges; functional ping of mutagenesis data; assessing the complementarity of the hypothetical structure's secondary structure and the secondary structures predicted for the sequence; insuring that critical electrostatic interactions are preserved; identifying sites of van der Waals clashes; and evaluating the sequence-structure-sequence similarity.

16. The method of claim 1 or 4, wherein the three-dimensional structural information comprises a three-dimensional structure of the macromolecule having a resolution of about 2–5 Angstroms.

17. A method of determining the tertiary structure of a protein, comprising the steps of:
(a) cross-linking residues of the protein such that the number of cross-links in the protein is at least about 10% of the number of amino acid residues in the protein;
(b) fragmenting the cross-linked protein into molecular fragments;
(c) subjecting the fragments to a mass spectrometry identification procedure;
(d) analyzing identification information obtained from the identification procedure to identify distance constraint information about residues in the protein and associated with the cross-linking; and
(e) applying the distance constrain information associated with the crosslinking to candidate three-dimensional conformations to rank said three three-dimensional conformations and selecting one or more of said conformations based on the rankings, wherein the tertiary structure is thereby determined.

18. The method of claim 17, wherein the one or more three dimensional conformations selected in (e) have resolutions of about 2–5 Angstroms.

19. The method of claim 17, wherein analyzing identification information obtained from the identification analysis comprises constructing a virtual library of proteolyzed products.

20. The method of claim 17, further comprising, prior to applying the distance constrain information associated with the cross-linking to the candidate three-dimensional conformations, performing an initial selection of the candidate three-dimensional conformations by assessing said conformations' compatibility with computed physical properties for the conformations.

21. The method of claim 20, wherein assessing said conformations' compatibility with computed physical properties for the conformation comprises using at least one technique selected from among: calculating the distribution of hydrophobic/hydrophilic amino acids; mapping a hydrogen-bond network; locating disulfide bridges; functional mapping of mutagenesis data; assessing the complementarity of the hypothetical structure's secondary structure and the secondary structures predicted for the sequence; insuring that critical electrostatic interactions are preserved; identifying sites of van der Waals clashes; and evaluating the sequence-structure sequence similarity.

* * * * *

SEQUENCE LISTING

```
<160> NUMBER OF SEQ ID NOS: 7

<210> SEQ ID NO 1
<211> LENGTH: 14
<212> TYPE: PRT
<213> ORGANISM: Human

<400> SEQUENCE: 1

Tyr Leu Ala Met Lys Glu Asp Gly Arg Leu Leu Ala Ser Lys
1               5                   10

<210> SEQ ID NO 2
<211> LENGTH: 9
<212> TYPE: PRT
<213> ORGANISM: hUMAN

<400> SEQUENCE: 2

Thr Gly Gln Tyr Lys Leu Gly Pro Lys
1               5

<210> SEQ ID NO 3
<211> LENGTH: 16
<212> TYPE: PRT
<213> ORGANISM: Human
```

```
<400> SEQUENCE: 3

Glu Lys Ser Asp Pro His Ile Lys Leu Gln Leu Gln Ala Glu Glu Arg
 1               5                   10                  15

<210> SEQ ID NO 4
<211> LENGTH: 10
<212> TYPE: PRT
<213> ORGANISM: Human

<400> SEQUENCE: 4

Leu Tyr Lys Asn Gly Gly Phe Phe Leu Arg
 1               5                   10

<210> SEQ ID NO 5
<211> LENGTH: 8
<212> TYPE: PRT
<213> ORGANISM: Human

<400> SEQUENCE: 5

Glu Lys Ser Asp Pro His Ile Lys
 1               5

<210> SEQ ID NO 6
<211> LENGTH: 153
<212> TYPE: PRT
<213> ORGANISM: Human

<400> SEQUENCE: 6

Ala Pro Val Arg Ser Leu Asn Cys Thr Leu Arg Asp Ser Gln Gln Lys
 1               5                   10                  15

Ser Leu Met Val Met Ser Gly Pro Tyr Glu Leu Lys Ala Leu His Leu
                20                  25                  30

Gln Gly Gln Asp Met Glu Gln Gln Val Val Phe Ser Met Ser Phe Val
            35                  40                  45

Gln Gly Glu Glu Ser Asn Asp Lys Ile Pro Val Ala Leu Gly Lys Glu
        50                  55                  60

Lys Asn Leu Tyr Leu Ser Cys Val Leu Lys Asp Asp Lys Pro Thr Leu
 65                  70                  75                  80

Gln Leu Glu Ser Val Asp Pro Lys Asn Tyr Pro Lys Lys Lys Met Glu
                85                  90                  95

Lys Arg Phe Val Phe Asn Lys Ile Glu Ile Asn Asn Lys Leu Glu Phe
                100                 105                 110

Glu Ser Ala Gln Phe Pro Asn Trp Tyr Ile Ser Thr Ser Gln Ala Glu
            115                 120                 125

Asn Met Pro Val Phe Leu Gly Gly Thr Lys Gly Gly Gln Asp Ile Thr
        130                 135                 140

Asp Phe Thr Met Gln Phe Val Ser Ser
145                 150

<210> SEQ ID NO 7
<211> LENGTH: 145
<212> TYPE: PRT
<213> ORGANISM: Human

<400> SEQUENCE: 7

Pro Ala Leu Pro Glu Asp Gly Gly Ser Gly Ala Phe Pro Pro Gly His
 1               5                   10                  15

Phe Lys Asp Pro Lys Arg Leu Tyr Cys Lys Asn Gly Gly Phe Phe Leu
                20                  25                  30
```

```
Arg Ile His Pro Asp Gly Arg Val Asp Gly Val Arg Glu Lys Ser Asp
        35              40              45
His Ile Lys Leu Gln Leu Gln Ala Glu Glu Arg Gly Val Val Ser Ile
    50              55              60
Lys Gly Val Cys Ala Asn Arg Tyr Leu Ala Met Lys Glu Asp Gly Arg
65              70              75                      80
Leu Leu Ala Ser Lys Cys Val Thr Asp Glu Cys Phe Phe Phe Glu Arg
            85              90                      95
Leu Glu Ser Asn Asn Tyr Asn Thr Tyr Arg Ser Arg Lys Tyr Ser Ser
            100             105             110
Trp Tyr Val Ala Leu Lys Arg Thr Gly Gln Tyr Lys Leu Gly Pro Lys
        115             120             125
Thr Gly Pro Gly Gln Lys Ala Ile Leu Phe Leu Pro Met Ser Ala Lys
    130             135             140
Ser
145
```